(12) United States Patent
Morrissey et al.

(10) Patent No.: US 9,597,375 B2
(45) Date of Patent: *Mar. 21, 2017

(54) COAGULATION AND FIBRINOLYTIC CASCADES MODULATOR

(75) Inventors: James H. Morrissey, Champaign, IL (US); Stephanie A. Smith, Champaign, IL (US); Roberto Docampo, Athens, GA (US); Nicola J. Mutch, Urbana, IL (US)

(73) Assignee: The Board of Trustees of the University of Illinios, Urbana, IL (US)

( * ) Notice: Subject to any disclaimer, the term of this patent is extended or adjusted under 35 U.S.C. 154(b) by 1999 days.

This patent is subject to a terminal disclaimer.

(21) Appl. No.: 12/582,595

(22) Filed: Oct. 20, 2009

(65) Prior Publication Data

US 2010/0143492 A1    Jun. 10, 2010

Related U.S. Application Data

(63) Continuation of application No. 11/362,270, filed on Feb. 23, 2006, now Pat. No. 7,682,808.

(60) Provisional application No. 60/658,776, filed on Mar. 4, 2005.

(51) Int. Cl.
*A61K 38/36* (2006.01)
*C12Q 1/56* (2006.01)
*G01N 33/86* (2006.01)

(52) U.S. Cl.
CPC .......... *A61K 38/36* (2013.01); *C12Q 1/56* (2013.01); *G01N 33/86* (2013.01)

(58) Field of Classification Search
CPC .......... A61K 38/36; C12Q 1/56; G01N 33/86
See application file for complete search history.

(56) References Cited

U.S. PATENT DOCUMENTS

| | | | |
|---|---|---|---|
| 3,983,004 A | 9/1976 | Trobisch et al. | |
| 4,139,619 A | 2/1979 | Chidsey, III | |
| 4,416,812 A | 11/1983 | Becker et al. | |
| 4,684,635 A | 8/1987 | Orentreich et al. | |
| 4,784,944 A | 11/1988 | Kolde | |
| 4,865,984 A | 9/1989 | Nemerson et al. | |
| 4,874,766 A * | 10/1989 | Ooms et al. ............ | 514/266.23 |
| 5,059,525 A | 10/1991 | Bartl et al. | |
| 5,169,786 A | 12/1992 | Carroll et al. | |

(Continued)

FOREIGN PATENT DOCUMENTS

| | | |
|---|---|---|
| DE | 1617733 | 4/1971 |
| EP | 0 727 434 | 8/1996 |

(Continued)

OTHER PUBLICATIONS

Smith, S.A. et al., "Polyphosphate enhances fibrin clot structure", Blood, vol. 112, No. 7, pp. 2810-2816, (2008).

(Continued)

*Primary Examiner* — Christina Bradley
(74) *Attorney, Agent, or Firm* — Lathrop & Gage LLP

(57) ABSTRACT

Methods for stopping or slowing bleeding from a wound are provided; these methods include the step of administering a composition comprising a polyphosphate (polyP) to blood from the wound at the site of the wound. Also provided are methods for slowing fibrinolysis and for blocking the action of Tissue Factor Pathway Inhibitor (TFPI) with the use of polyP.

8 Claims, 15 Drawing Sheets

(56) References Cited

U.S. PATENT DOCUMENTS

| | | | |
|---|---|---|---|
| 5,192,689 A | 3/1993 | Hemker et al. | |
| 5,254,350 A | 10/1993 | Barrow et al. | |
| 5,270,451 A | 12/1993 | Hawkins et al. | |
| 5,298,599 A | 3/1994 | Rezaie et al. | |
| 5,314,695 A | 5/1994 | Brown | |
| 5,338,538 A | 8/1994 | Tricca et al. | |
| 5,358,853 A | 10/1994 | Butler et al. | |
| 5,391,380 A | 2/1995 | Barrow et al. | |
| 5,418,141 A | 5/1995 | Zweig et al. | |
| 5,418,143 A | 5/1995 | Zweig | |
| 5,426,031 A | 6/1995 | Hawkins et al. | |
| 5,472,850 A | 12/1995 | Morrissey | |
| 5,504,067 A | 4/1996 | Morrissey et al. | |
| 5,504,193 A | 4/1996 | Hawkins et al. | |
| 5,508,170 A | 4/1996 | Butler et al. | |
| 5,512,304 A | 4/1996 | Barrow et al. | |
| 5,580,744 A | 12/1996 | Zweig | |
| 5,599,909 A | 2/1997 | Fickenscher et al. | |
| 5,625,036 A | 4/1997 | Hawkins et al. | |
| 5,632,727 A * | 5/1997 | Tipton et al. | 602/47 |
| 5,691,380 A | 11/1997 | Mason et al. | |
| 5,705,477 A * | 1/1998 | Sporn et al. | 424/443 |
| 5,741,658 A | 4/1998 | Morrissey | |
| 5,787,901 A | 8/1998 | Wilson | |
| 5,858,724 A | 1/1999 | Novy, Jr. et al. | |
| 5,866,425 A | 2/1999 | Woodhams et al. | |
| 5,888,968 A | 3/1999 | Chen et al. | |
| 5,945,087 A | 8/1999 | Nelson et al. | |
| 5,968,528 A | 10/1999 | Deckner et al. | |
| 6,100,072 A | 8/2000 | Brucato et al. | |
| 6,187,347 B1 | 2/2001 | Patterson et al. | |
| 6,194,394 B1 | 2/2001 | Hawkins | |
| 6,248,353 B1 | 6/2001 | Singh | |
| 6,258,368 B1 | 7/2001 | Beerse et al. | |
| 6,261,803 B1 | 7/2001 | Zander et al. | |
| 6,319,896 B1 | 11/2001 | Dorin et al. | |
| 6,323,326 B1 | 11/2001 | Dorin et al. | |
| 6,355,858 B1 * | 3/2002 | Gibbins | 602/41 |
| 6,376,209 B2 | 4/2002 | Wissel et al. | |
| 6,391,609 B1 | 5/2002 | Goldford | |
| 6,432,657 B1 | 8/2002 | Kikuchi et al. | |
| 6,451,610 B1 | 9/2002 | Gorman et al. | |
| 6,509,050 B1 | 1/2003 | Henson et al. | |
| 6,528,273 B2 | 3/2003 | Hawkins | |
| 6,706,861 B2 | 3/2004 | Singh et al. | |
| 6,733,985 B1 | 5/2004 | Lee | |
| 6,815,424 B2 | 11/2004 | Vickery et al. | |
| 7,148,067 B2 | 12/2006 | Morrissey et al. | |
| 7,622,737 B2 | 11/2009 | Farooq et al. | |
| 7,682,808 B2 | 3/2010 | Morrissey et al. | |
| 2001/0004641 A1 | 6/2001 | Hawkins | |
| 2001/0043951 A1* | 11/2001 | Kim et al. | 424/601 |
| 2002/0012699 A1 | 1/2002 | Singh et al. | |
| 2002/0012958 A1 | 1/2002 | Wissel et al. | |
| 2002/0019021 A1 | 2/2002 | Kraus | |
| 2002/0132370 A1 | 9/2002 | Lassen et al. | |
| 2002/0151646 A1 | 10/2002 | Kikukawa et al. | |
| 2002/0182225 A1 | 12/2002 | Wang et al. | |
| 2003/0064414 A1 | 4/2003 | Benecky et al. | |
| 2003/0153084 A1 | 8/2003 | Zheng et al. | |
| 2003/0211460 A1 | 11/2003 | Nelsestuen | |
| 2004/0037893 A1 | 2/2004 | Hansen et al. | |
| 2004/0043933 A1 | 3/2004 | Hansen et al. | |
| 2004/0084867 A1 | 5/2004 | Leyland-Jones | |
| 2004/0086953 A1 | 5/2004 | Jenny et al. | |
| 2006/0088524 A1 | 4/2006 | Morrissey et al. | |
| 2006/0198837 A1 | 9/2006 | Morrissey et al. | |
| 2008/0260858 A1 | 10/2008 | Morrissey et al. | |
| 2009/0053288 A1 | 2/2009 | Eskridge, Jr. et al. | |
| 2010/0284998 A1 | 11/2010 | Smith et al. | |
| 2010/0297257 A1 | 11/2010 | Smith et al. | |

FOREIGN PATENT DOCUMENTS

| | | |
|---|---|---|
| EP | 0 942 284 | 9/1999 |
| WO | WO 93/07492 | 4/1993 |
| WO | WO 98/44352 | 10/1998 |
| WO | WO 99/15196 | 4/1999 |
| WO | 99/43810 | 9/1999 |
| WO | WO 00/62742 | 10/2000 |
| WO | WO 00/64471 | 11/2000 |
| WO | WO 00/70084 | 11/2000 |
| WO | WO 2004/094475 | 11/2004 |
| WO | WO 2004/110462 | 12/2004 |
| WO | WO 2005/031303 | 4/2005 |
| WO | WO 2006/031387 | 3/2006 |
| WO | WO 2006/088741 | 8/2006 |
| WO | WO 2006/096345 | 9/2006 |
| WO | WO 2009/046194 | 4/2009 |
| WO | WO 2009/061697 | 5/2009 |

OTHER PUBLICATIONS

Allen, D., "Clotting agents buy wounded troops life-saving time", Stars and Stripes, 3 pages, (2003).

International Search Report dated Feb. 10, 2010 for PCT application No. PCT/US2008/078584.

Gibble, et al., "Fibrin glue: the perfect operative sealant?", Transfusion, vol. 30, No. 8, XP002561966, pp. 741-747, (1990).

Prosecution history for related U.S. Appl. No. 11/816,401, filed Apr. 2, 2008 (downloaded Apr. 17, 2012), last document dated Apr. 11, 2012, 56 pp.

Prosecution history for related U.S. Appl. No. 12/680,947, filed Jun. 21, 2010 (downloaded Apr. 17, 2012), last document dated Mar. 8, 2012, 34 pp.

Choi et al. (2010) "Phosphoramidate end labeling of inorganic polyphosphates: Facile manipulation of polyphosphate for investigating and modulating its biological activities," Biochemistry 49:9935-9941.

Choi et al. (2011) "Polyphosphate is a Cofactor for the Activation of Factor XI by Thrombin," Blood 118:6963-6970.

Müller et al. (2009) "Platelet Polyphosphates Are Proinflammatory and Procoagulant Mediators In Vivo," Cell 139:1143-1156.

Mutch et al. (2010) "Polyphosphate Binds with High Affinity to Exosite II of Thrombin," J Thromb Haemost 8:548-555.

Semeraro et al. (2011) Extracellular Histones Promote Thrombin Generation Through Platelet-Dependent Mechanisms: Involvement of Platelet TLR2 and TLR4, Blood 118:1952-1961.

Smith et al. (2010) "Polyphosphate Exerts Differential Effects on Blood Clotting, Depending on Polymer Size," Blood 116:4353-4359.

Yun et al. (2009) "Polyphosphate and Omptins: Novel Bacterial Procoagulant Agents," J Cell Molec Med 13:4146-4153.

Noegel, et al., "Isolation of a high molecular weight polyphosphate from Neisseria gonorrhoeae", J. Exp. Med., 157, 2049-2060, (1983).

"Clotting agents buy wounded troops life-saving time" by David Allen in Stars and Stripes, Apr. 13, 2003.

Bajzar, L., et al., "TAFI, or plasma procarboxypeptidase B, couples the coagulation and fibrinolytic cascades through the thrombin-thrombomodulin complex"., Journal of Biological Chemistry, vol. 271, No. 28, pp. 16603- 16608, (1996).

Bajzar, L., et al., "Thrombin activatable fibrinolysis inhibitor: not just an inhibitor of fibrinolysis"., Crit. Care Med., vol. 32, pp. S320-S324, (2004).

Banner, D.W., et al., "The crystal structure of the complex of blood coagulation factor VIIa with soluble tissue factor"., Nature, vol. 380, pp. 41-46, (1996).

Barrowcliffe, T.W., et al.,"Studies of phospholipid reagents used in coagulation I: Some general properties and their sensitivity to factor VIII"., Thrombosis and Haemostasis, Stuttgart, DE, vol. 46, No. 3, pp. 629-633, (1981).

(56) References Cited

OTHER PUBLICATIONS

Bladbjerg, E. M., et al., "In vitro effects of heparin and tissue factor pathway inhibitor on factor VII assays. Possible implications for measurements in vivo after heparin therapy"., Blood Coagulation and Fibrinolysis, vol. 11, No. 8, pp. 739-745, (2000).
Boffa, M. B., et al., "Roles of thermal instability and proteolytic cleavage in regulation of activated thrombin-activable fibrinolysis inhibitor"., J Biol. Chem., vol. 275, pp. 12868-12878, (2000).
Broze, G. J., Jr. "Tissue factor pathway inhibitor"., Thromb. Haemost., vol. 74, pp. 90-93, (1995).
Camerer, E., et al., "Notes on the cell biology of tissue factor"., Haemostasis, vol. 26, pp. 25-30, (1996).
Chikh, G.G., et al., "Attaching histidine-tagged peptides and proteins to lipid-based carriers through use of metal-ion-chelating lipids"., Biochem. Biophys. Acta, vol. 1567, pp. 204-212, (2002).
Cornell, B.A., et al., "Tethered-bilayer lipid membranes as a support for membrane-active peptides"., Biochem. Soc. Trans., vol. 29, pp. 613-617, (2001).
Dano, K., et al., "Plasminogen activators, tissue degradation, and cancer"., Adv. Cancer Res., vol. 44, pp. 139-266, (1985).
Darst, S.A., "A new twist on protein crystallization"., Proc. Natl. Acad. Sci. USA, vol. 95, pp. 7848-7849, (1998).
Docampo, R., et al., "Acidocalcisomes—conserved from bacteria to man"., Nature Rev. Microbiol., vol. 3, pp. 251-261, (2005).
Fiore, M.M., et al., "The biochemical basis for the apparent defect of soluble mutant tissue factor in enhancing the proteolytic activities of factor VIIa"., J. Biol. Chem., vol. 269, pp. 143-149, (1994).
Fiore, M.M., et al., "An unusual antibody that blocks tissue factor/factor VIIa function by inhibiting cleavage only of macromolecular substrates"., Blood, vol. 80, pp. 3127-3134, (1992).
Gemmell, C.H., et al., "Flow as a regulator of the activation of factor X by tissue factor"., Blood, vol. 72, pp. 1404-1406, (1988).
Gemmell, C.H., et al., "The effects of shear rate on the enzymatic activity of the tissue factor-factor VIIa complex"., Microvasc. Res., vol. 40, pp. 327-340, (1990).
Gemmell, C.H., et al., "Utilization of a continuous flow reactor to study the lipoprotein-associated coagulation inhibitor (LACI) that inhibits tissue factor"., Blood, vol. 76, pp. 2266-2271, (1990).
Groves, J.T., et al., "Supported planar bilayers in studies on immune cell adhesion and communication"., J. Immunol. Methods, vol. 278, pp. 19-32, (2003).
Hansen, J-B., et al., "Reduction of factor FVIIa activity during heparin therapy evidence for assay interactions with tissue factor pathway inhibitor and antithrombin"., Thrombosis Research, vol. 100, pp. 389-396, (2000).
International Search Report dated Mar. 1, 2006 for corresponding PCT application No. PCT/US2005/029873.
Jeong, S.W., et al., "Synthesis of a polymerizable metal-ion-chelating lipid for fluid bilayers"., J. Org. Chem., vol. 66, No. 14, pp. 4799-4802, (2001).
Jones, D.T., "Do transmembrane protein superfolds exist?", FEBS Letters, vol. 423, pp. 281-285, (1998).
Kent, M.S., et al., "Segment concentration profile of myoglobin adsorbed to metal ion chelating lipid monolayers at the air-water interface by neutron reflection"., Langmuir, vol. 18, No. 9, pp. 3754-3757, (2002).
Kornberg, A. "Inorganic polyphosphate: Toward making a forgotten polymer unforgettable"., Journal of Bacteriology, vol. 177, No. 3, pp. 491-496, (1995).
Kubalek, E.W., et al., "Two-dimensional crystallization of histidine-tagged, HIV-1 reverse transcriptase promoted by a novel nickel-chelating lipid"., J. Structural Biology, vol. 113, pp. 117-123, (1994).
Lauer, S.A., et al., "Development and characterization of Ni-NTA-bearing microspheres"., Cytometry, vol. 48, pp. 136-145, (2002).
Lazarus, R.A., et al., "Inhibitors of Tissue Factor*Factor VIIa for anticoagulant therapy"., Curr. Med. Chem., vol. 11, pp. 2275-2290, (2004).
Linkins, L.A., et al., "New anticoagulant therapy"., Annu. Rev. Med., vol. 56, pp. 63-77, (2005).

Lorenz, B., et al., "Mammalian intestinal alkaline phosphatase acts as highly active exopolyphosphatase"., Biochim. Biophys. Acta, vol. 1547, pp. 254-261, (2001).
Lorenz, B., et al., "Anti-HIV-1 activity of inorganic polyphosphates"., J. Acquir. Immune. Defic. Syndr. Hum. Retrovirol., vol. 14, pp. 110-118, (1997).
Marx, P.F., et al., "Inactivation of active thrombin-activable fibrinolysis inhibitor takes place by a process that involves conformational instability rather than proteolytic cleavage"., J. Biol. Chem., vol. 275, pp. 12410-12415, (2000).
Marx, P.F., et al., "Plasmin-mediated activation and inactivation of thrombin-activatable fibrinolysis inhibitor"., Biochemistry, vol. 41, pp. 6688-6696, (2002).
Morrissey, J.H., "Tissue factor and factor VII initiation of coagulation". In: Colman RW, Hirsh J, Marder VJ, Clowes AW, George JN, editors, Hemostasis and Thrombosis: Basic Principles and Clinical Practice, Philadelphia, Lippincott Williams & Wilkins, pp. 89-101, (2001).
Morrissey, J.H., et al., "Quantitation of activated factor VII levels in plasma using a tissue factor mutant selectively deficient in promoting factor VII activation"., Blood, vol. 81, pp. 734-744, (1993).
Morrissey, J.H., et al., "Factor VIIa-tissue factor: functional importance of protein-membrane interactions"., Thromb. Haemost., vol. 78, pp. 112-116, (1997).
Morrissey, J.H., et al., "Monoclonal antibody analysis of purified and cell-associated tissue factor"., Thromb. Research, vol. 52, pp. 247-261, (1988).
Mosnier, L.O., et al., "Identification of thrombin activatable fibrinolysis inhibitor (TAFI) in human platelets"., Blood, vol. 101, pp. 4844-4846, (2003).
Nakagaki, T., et al., "Initiation of the extrinsic pathway of blood coagulation: evidence for the tissue factor dependent autoactivation of human coagulation factor VII"., Biochemistry, vol. 30, pp. 10819-10824, (1991).
Nemerson, Y., et al., "Tissue factor accelerates the activation of coagulation factor VII: The role of a bifunctional coagulation cofactor"., Thromb. Res., vol. 40, pp. 351-358, (1985).
Nesheim, M., "Thrombin and fibrinolysis"., Chest, vol. 124, No. 3, pp. 33S-39S, (2003).
Nesheim, M., et al., "Thrombin, thrombomodulin and TAFI in the molecular link between coagulation and fibrinolysis"., Thromb. Haemost, vol. 78, pp. 386-391, (1997).
Neuenschwander, P.F., et al., "Roles of the membrane-interactive regions of factor VIIa and tissue factor. The factor VIIa Gla domain is dispensable for binding to tissue factor but important for activation of factor X"., J. Biol. Chem., vol. 269, pp. 8007-8013, (1994).
Neuenschwander, P.F., et al., "Deletion of the membrane anchoring region of tissue factor abolishes autoactivation of factor VII but not cofactor function. Analysis of a mutant with a selective deficiency in activity"., J. Biol. Chem., vol. 267, pp. 14477-14482, (1992).
Neuenschwander, P.F., et al., "Factor VII autoactivation proceeds via interaction of distinct protease-cofactor and zymogen-cofactor complexes. Implications of a two-dimensional enzyme kinetic mechanism"., J. Biol. Chem., vol. 268, pp. 21489-21492, (1993).
Nilsson, J., et al., "Comparative analysis of amino acid distributions in integral membrane proteins from 107 genomes"., Proteins, vol. 60, pp. 606-618, (2005).
Novotny, W.F., et al., "Platelets secrete a coagulation inhibitor functionally and antigenically similar to the lipoprotein associated coagulation inhibitor"., Blood, vol. 72, pp. 2020-2025, (1988).
Paborsky, L.R., et al., "Lipid association, but not the transmembrane domain, is required for tissue factor activity. Substitution of the transmembrane domain with a phosphatidylinositol anchor"., J. Biol. Chem., vol. 266, pp. 21911-21916, (1991).
Repke, D., et al., "Hemophilia as a defect of the tissue factor pathway of blood coagulation: effect of factors VIII and IX on factor X activation in a continuous-flow reactor"., Proc. Natl. Acad. Sci. USA, vol. 87, pp. 7623-7627, (1990).
Rojkjaer, R., et al., "Activation of the plasma kallikrein/kinin system on endothelial cell membranes"., Immunopharmacology, vol. 43, pp. 109-114, (1999).

(56) References Cited

OTHER PUBLICATIONS

Ruf, W., et al., "Phospholipid-independent and -dependent interactions required for tissue factor receptor and cofactor function"., J. Biol. Chem., vol. 266, pp. 2158-2166, (1991).
Ruiz, F.A., et al., "Human platelet dense granules contain polyphosphate and are similar to acidocalcisomes of bacteria and unicellular eukaryotes"., Journal of Biological Chemistry, vol. 279, No. 43, pp. 44250-44257, (2004).
Sandset, P. M., et al., "Heparin induces release of extrinsic coagulation pathway inhibitor (EPI)"., Thromb. Res., vol. 50, pp. 803-813, (1988).
Schneider, M., et al., "Two naturally occurring variants of TAFI (Thr-325 and Ile-325) differ substantially with respect to thermal stability and antifibrinolytic activity of the enzyme"., J. Biol. Chem., vol. 277, pp. 1021-1030, (2002).
Seddon, A.M., et al., "Membrane proteins, lipids and detergents: not just a soap opera"., Biochim. Biophys. Acta., vol. 1666, pp. 105-117, (2004).
Shigematsu, Y., et al., "Expression of human soluble tissue factor in yeast and enzymatic properties of its complex with factor VIIa"., J. Biol. Chem., vol. 267, pp. 267, pp. 21329-21337, (1992).
Smith, S.A., et al., "Properties of recombinant human thromboplastin that determine the International Sensitivity Index (ISI)"., J. Thromb. Haemost, vol. 2, pp. 1610-1616, (2004).
Smith, A., et al., "Properties of recombinant human thromboplastin that determine sensitivity to vitamin K-dependent coagulation factors"., Blood, vol. 104, No. 11, part 1, pp. 155A, 46th Annual meeting of the American Society of Hematology, San Diego, CA, USA, Dec. 4-7, 2004.
Terpe, K., "Overview of tag protein fusions: from molecular and biochemical fundamentals to commercial systems"., Appl. Microbiol. Biotechnol., vol. 60, pp. 523-533, (2003).
Tripodi, A., et al., "Recombinant tissue factor as substitute for conventional thromboplastin in the prothrombin time test"., Thromb. Haemost, vol. 67, pp. 42-45, (1992).
Wallin, E., et al., "Genome-wide analysis of integral membrane proteins from eubacterial, archaean, and eukaryotic organisms"., Protein Sci., vol. 7, pp, 1029-1038, (1998).
Waters, E.K., et al., "Restoring full biological activity to the isolated ectodomain of an integral membrane protein"., Biochemistry, vol. 45, No. 11, pp. 3769-3774, (2006).
Waxman, E., et al., "Human factor VIIa and its complex with soluble tissue factor: Evaluation of asymmetry and conformational dynamics by ultracentrifugation and fluorescence anisotropy decay methods"., Biochemistry, vol. 32, pp. 3005-3012, (1993).
Waxman, E., et al., "Tissue factor and its extracellular soluble domain: The relationship between intermolecular association with factor VIIa and enzymatic activity of the complex"., Biochemistry, vol. 31, pp. 3998-4003, (1992).
Jackson, C.M., "Monitoring oral anticoagulant therapy-INR values for the Owren prothrombin time"., Thromb Haemost, vol. 91, pp. 210-212, (2004).
Stone, M.J., et al., "Recombinant soluble human tissue factor secreted by *Saccharomyces cerevisiae* and refolded from *Escherichia coli* inclusion bodies: glycosylation of mutants, activity and physical characterization"., J. Biochem., vol. 310, pp. 605-614, (1995).
Bader, R., et al., "Multicentric evaluation of a new PT reagent based on recombinant human tissue factor and synthetic phospholipids"., Thrombosis and Haemostasis, vol. 71, No. 3, pp. 292-299, (1994).
Hirsh, J., et al., "American Heart Association/American College of Cardiology Foundation guide to warfarin therapy"., Circulation, vol. 107, pp. 1692-1711, (2003).
Hoots, K., Disseminated Intravascular Coagulation (DIC), Minutes from Jun. 18, 2004 meeting, pp. 1-6.
Kemball-Cook, G., et al., "High-level production of human blood coagulation factors VII and XI using a new mammalian expression vector"., Gene, vol. 139, pp. 275-279, (1994).
Kitchen, S., et al., "Two recombinant tissue factor reagents compared to conventional thromboplastins for determination of international normalised ratio: a thirty-three-laboratory collaborative study"., The Steering Committee of the UK National External Quality Assessment Scheme for Blood Coagulation., Thrombosis and Haemostasis, vol. 76, No. 3, pp. 372-376, (1996).
Kitchen, S., et al., "Standardization of prothrombin time for laboratory control of oral anticoagulant therapy"., Seminars in Thrombosis and Hemostasis, vol. 25, No. 1, pp. 17-25, (1999).
Massignon, D., et al., "Prothrombin time sensitivity and specificity to mild clotting factor deficiencies of the extrinsic pathway: evaluation of eight commercial thromboplastins"., Thrombosis and Haemostasis, vol. 75, No. 4, pp. 590-594, (1996).
Morrison, M., et al., "Discrepant INR values: a comparison between Manchester and Thrombotest reagents using capillary and venous samples"., Clin. Lab. Haemat., vol. 11, No. 4, pp. 393-398, (1989).
Morrissey, J.H., et al., "Molecular cloning of the cDNA for tissue factor, the cellular receptor for the initiation of the coagulation protease cascade"., Cell, vol. 50, pp. 129-135, (1987).
Morrissey JH. Tissue factor: an enzyme cofactor and a true receptor. Thromb Haemost 2001; 86:66-74.
Neuenschwander, P.F., et al., "Phosphatidylethanolamine augments factor VIIa-Tissue factor activity: Enhancement of sensitivity to phosphatidylserine"., Biochemistry, vol. 34, No. 43, pp. 13988-13993, (1995).
Poller, L., et al., "Minimum lyophilized plasma requirement for ISI calibration"., European Concerted Action on Anticoagulation, Am. J. Clin. Pathol., vol. 109, pp. 196-204, (1998).
Poller, L., "International Normalized Ratios (INR): the first 20 years"., Journal of Thrombosis and Haemostasis, vol. 2, pp. 849-860, (2004).
Rezaie, A.R., et al., "Expression and purification of a soluble tissue factor fusion protein with an epitope for an unusual calcium-dependent antibody"., Protein Expression and Purification, vol. 3, pp. 453-460, (1992).
Roussi, J., et al., "French multicentric evaluation of recombinant tissue factor (recombiplastin) for determination of prothrombin time"., Thrombosis and Haemostasis, vol. 72, No. 5, pp. 698-704, (1994).
Search from USPTO website dated May 26, 2004, for key words "Factor VII" and thromboplastin.
Search from USPTO website dated May 27, 2004, for key words "Factor VII" and thromboplastin, PGPUB Production Database.
Smith, S.A., et al., "Rapid and efficient incorporation of tissue factor into liposomes"., Journal of Thrombosis and Haemostasis, vol. 2, pp. 1155-1162, (2004).
Testa, S., et al.,"Discrepant sensitivity of thromboplastin reagents to clotting factor levels explored by the prothrombin time in patients on stable oral anticoagulant treatment: impact on the international normalized ratio system"., Haematologica, vol. 87, No. 12, pp. 1265-1273, (2002).
Van Den Besselaar, A.M.H.P., et al., "Annex 3: Guidelines for thromboplastins and plasma used to control oral anticoagulant therapy"., World Health Organization, Technical Report Series, No. 889, pp. 64-93, (1999).
Watson, C., et al., "Recombinant and tissue extract thromboplastins for determination of international normalised ratio in over-anticoagulated patients"., British Journal of Biomedical Science, vol. 56, pp. 123-127, (1999).
Zwaal, R.F., "Membrane and lipid involvement in blood coagulation"., Biochim Biophys Acta, vol. 515, pp. 163-205, (1978).
Abstract of: Smith, S.A., et al.,"Do elevated plasma tissue factor pathway inhibitor (TFPI) levels affect measurement of factor VIIa?"., Blood, vol. 104, Issue 11, (2004).
Abstract of: Smith, S.A., et al., "Polyphosphates—A novel modulator of coagulation"., Arteriosclerosis, Thrombosis, and Vascular Biology, Journal of the American Heart Association, Abstracts of the 6th Annual Conference on arteriosclerosis, Thrombosis and Vascular Biology, vol. 25, 4 pages, (2005).
Bouma, B.N., et al., Thrombin-activatable fibrinolysis inhibitor (TAFI, plasma procarboxypeptidase B, procarboxypeptidase R, procarboxypeptidase U)., Journal of Thrombosis and Haemostasis, vol. 1, pp. 1566-1574, (2003).
International Search Report dated Oct. 5, 2006 for PCT application No. PCT/US2006/006642.

(56) References Cited

OTHER PUBLICATIONS

Smith, S.A., et al., "Polyphosphate modulates blood coagulation and fibrinolysis"., PNAS, vol. 103, No. 4, pp. 903-908, (2006).
International Search Report dated Dec. 22, 2006 for PCT application No. PCT/US2006/004789.
Radler, U. et al., "Design of supported membranes tethered via metal-affinity ligand-receptor pairs", Biophysical Journal, vol. 79, pp. 3144-3152, (2000).
Shrout, A.L. et al., "Template-directed assembly of receptor signaling complexes", Biochemistry, vol. 42, No. 46, pp. 13379-13385, (2003).
Wolberg, A.S., "Thrombin generation and fibrin clot structure", Blood Reviews, 21, pp. 131-142, (2007).
DiStasio, E., et al., "CI—Regulates the Structure of the Fibrin Clot", Biophysical Journal, vol. 75, pp. 1973-1979, (1998).
Nair, C.H., et al., "Effect of Temperature, pH and Ionic Strength and Composition on Fibrin Network Structure and Its Development", Thrombosis Research, 42, pp. 809-816, (1986).
Carr Jr., M.E., et al., "Influence of Ca2+ on the structure of reptilase-derived and thrombin-derived fibrin gels", Biochem. J., 239, pp. 513-516, (1986).
Lauricella, A.M., et al., "Influence of homocysteine on fibrin network lysis", Blood Coagulation and Fibrinolysis, 17, pp. 181-186, (2006).
Dugan, T.A., et al., "Decorin Modulates Fibrin Assembly and Structure", The Journal of Biological Chemistry, vol. 281, No. 50, pp. 38208-38216, (2006).
Carr Jr., M.E., et al., "Effect of Glycosaminoglycans on Thrombin- and Atroxin-Induced Fibrin Assembly and Structure", Thrombosis Haemostasis, 62, pp. 1057-1061, (1989).
Parise, P., et al., "Effects of low molecular weight heparins on fibrin polymerization and clot sensitivity to t-PA-induced lysis", Blood Coagulation and Fibrinolysis, vol. 4, pp. 721-727, (1993).
Carr Jr., M.E., et al., "Dextran-Induced Changes in Fibrin Fiber Size and Density Based on Wavelength Dependence of Gel Turbidity", Macromolecules, 13, pp. 1473-1477, (1980).
Carr Jr., M.E., "Effect of hydroxyethyl starch on the structure of thrombin- and reptilase-induced fibrin gels", J. Lab. Clin. Med, 108, pp. 556-561, (1986).
Kornberg, A., et al., "Inorganic Polyphosphate: A Molecule of Many Functions", Annu.Rev.Biochem., 68, pp. 89-125, (1999).
Kulaev, I.S., et al., "Metabolism and Function of Polyphosphates in Bacteria and Yeast", Progress Molecular and Subcellular Biology, vol. 23, pp. 27-43, (1999).
Kumble, K.D., et al., "Inorganic Polyphosphate in Mammalian Cells and Tissues", The Journal of Biological Chemistry, vol. 270, No. 11, pp. 5818-5822, (1995).
Hernandez-Ruiz, L., et al., "Inorganic polyphosphate and specific induction of apoptosis in human plasma cells", The Hematology Journal, 91(9), pp. 1180-1186, (2006).
Kawazoe, Y., et al., "Induction of Calcification in MC3T3-E1 Cells by Inorganic Polyphosphate", J. Dent. Res., 83(8), pp. 613-618, (2004).
Han, K.Y., et al., "Polyphosphate blocks tumour metastasis via anti-angiogenic activity", Biochem. J., 406, pp. 49-55, (2007).
Wang, L., et al., "Inorganic polyphosphate stimulates mammalian TOR, a kinase involved in the proliferation of mammary cancer cells", Proc. Natl. Acad. Sci. U.S.A, vol. 100, No. 20, pp. 11249-11254, (2003).
Wolberg, A.S., et al., "Analyzing fibrin clot structure using a microplate reader", Blood Coagulation and Fibrinolysis, vol. 13, No. 6, pp. 533-539, (2002).
Wolberg, A.S., et al., "Elevated prothrombin results in clots with an altered fiber structure: a possible mechanism of the increased thrombotic risk", Blood, vol. 101, No. 8, pp. 3008-3013, (2003).
Yakovlev, S., et al., "Interaction of Fibrin(ogen) with Heparin: Further Characterization and Localization of the Heparin-Binding Site", Biochemistry, 42, pp. 7709-7716, (2003).
Collen, A., et al., "Unfractionated and Low Molecular Weight Heparin Affect Fibrin Structure and Angiogenesis in Vitro", Cancer Research, 60, pp. 6196-6200, (2000).
Carr Jr., M.E, et al. "Size and Density of Fibrin Fibers from Turbidity", Macromolecules, 11, pp. 46-50, (1978).
Mosesson, M.W., "Fibrinogen and fibrin structure and functions", Journal of thrombosis and Haemostasis, 3, pp. 1894-1904, (2005).
Wozniak, G., "Fibrin Sealants in supporting surgical techniques: the importance of individual components", Cardiovascular Surgery, vol. 11, No. S1, pp. 17-21, (2003).
Dickneite, G., et al., "A comparison of fibrin sealants in relation to their in vitro and in vivo properties", Thrombosis Research, 112, pp. 73-82, (2003).
Jackson, M.R., "Fibrin sealants in surgical practice: An overview", The American Journal of Surgery, 182, pp. 1S-7S, (2001).
Aledort, L.M., "Comparative thrombotic event incidence after infusion of recombinant factor VIIa versus factor VIII inhibitor bypass activity", Journal of Thrombosis and Haemostasis, 2, pp. 1700-1708, (2004).
Brody, D.L., et al., "Use of recombinant factor VIIa in patients with warfarin-associated intracranial hemorrhage", Neurocritical Care, 2, pp. 263-267, (2005).
Firozvi, K., et al., "Reversal of low-molecular-weight heparin-induced bleeding in patients with pre-existing hypercoagulable states with human recombinant activated factor VII concentrate", American Journal of Hematology, 81, pp. 582-589, (2006).
Gerotziafas, G.T., et al., "Recombinant factor VIIa partially reverses the inhibitory effect of fondaparinux on thrombin generation after tissue factor activation in platelet rich plasma and whole blood", Thromb. Haemost., 91, pp. 531-537, (2004).
Hoots, W.K., "Challenges in the Therapeutic use of a "So-Called" Universal Hemostatic Agent: Recombinant factor VIIa", American Society of Hematology, Educ.Program, pp. 426-431, (2006).
Kessler, C.M., "Current and future challenges of antithrombotic agents and anticoagulants: Strategies for reversal of hemorrhagic complications", Seminars in Hematology, 41, pp. 44-50, (2004).
Kornberg, A., et al., "Inorganic polyphosphate: a molecule of many functions", Annu. Rev. Biochem., 68, pp. 89-125, (1999).
Krishnamurthy, G.T., et al., "Clinical comparison of the kinetics of 99mTc-labeled polyphosphate and diphosphonate", Journal of Nuclear Medicine, 15(10), pp. 848-855, (1974).
Kubitza, D., et al., "Safety, pharmacodynamics, and pharmacokinetics of BAY 59-7939—an oral, direct Factor Xa inhibitor—after multiple dosing in healthy male subjects", Eur J Clin Pharmacol, 61, pp. 873-880, (2005).
Lin, J., et al., "The use of recombinant activated factor VII to reverse warfarin-induced anticoagulation in patients with hemorrhages in the central nervous system: preliminary findings", J. Neurosurg., 98, pp. 737-740, (2003).
Lisman, T., et al., "Recombinant factor VIIa reverses the in vitro and ex vivo anticoagulant and profibrinolytic effects of fondaparinux", Journal of Thrombosis and Haemostasis, 1, pp. 2368-2373, (2003).
Luddington, R.J., "Thromboelastography/Thrombelastometry", Clin. Lab. Haemost., 27, pp. 81-90, (2005).
Mathew, P., "Current Opinion on Inhibitor Treatment Options", Seminars in Hematology, 43, pp. S8-13, (2006).
O'Connell, K.A., et al., "Thromboembolic adverse events after use of recombinant human coagulation factor VIIa", JAMA, vol. 295, No. 3, pp. 293-298, (2006).
Oh, J.J., et al., "Recombinant factor VIIa for refractory bleeding after cardiac surgery secondary to anticoagulation with the direct thrombin inhibitor lepirudin", Pharmacotherapy, 26, No. 4, pp. 576-577, (2006).
Ruiz, F.A., et al., "Human platelet dense granules contain polyphosphate and are similar to acidocalcisomes of bacteria and unicellular eukaryotes", Journal of Biological Chemistry, vol. 279, No. 43, pp. 44250-44257, (2004).
Schulman, S., et al., "Anticoagulants and Their Reversal", Transfusion Medicine Reviews, vol. 21, No. 1, pp. 37-48, (2007).
Smith, S.A., et al., "Polyphosphate modulates blood coagulation and fibrinolysis", Proc. Natl. Acad. Sci. U.S.A., vol. 103, No. 4, pp. 903-908, (2006).

(56) References Cited

OTHER PUBLICATIONS

Young, G., et al., "Recombinant activated factor VII effectively reverses the anticoagulant effects of heparin, enoxaparin, fondaparinux, argatroban, and bivalirudin ex vivo as measured using thromboelastography", Blood Coagulation Fibrinolysis, 18, pp. 547-553, (2007).

Poller, L., "Activated partial thromboplastin time (APTT)", Laboratory Techniques in Thrombosis: A Manual (2nd revised edition of ECAT Assay Procedures), Kluwer Academic Publishers, Dordrecht, (1999).

Invitation to Pay Additional Fees and International Search Report for PCT application No. PCT/US2006/004789 dated Oct. 24, 2006.

Smith S.A. et al., "Sensitive fluorescence detection of polyphosphate in polyacrylamide gels using 4',6-diamidino-2-phenylindol", Electrophoresis, vol. 28, No. 19, pp. 3461-3465, (2007).

Colletier, J-P. et al., "Protein encapsulation in liposomes: efficiency depends on interactions between protein and phospholipid bilayer", BMC Biotechnology, vol. 2, pp. 1-8, (2002).

Smith, S.A. et al., "Polyphosphate enhances fibrin clot structure", Blood (ASH Annual Meeting Abstracts), 110: Abstract 403, (2007).

Smith, S.A. et al., "Polyphosphate shortens the clotting time of hemophilic and anticoagulated plasma", Blood (ASH Annual Meeting Abstracts), 110: Abstract 1760, (2007).

Smith, S.A. et al., "The various procoagulant effects of PolyP require different minimal polymer lengths", Blood (ASH Annual Meeting Abstracts), 110: Abstract 1761, 2007.

Dickneite, G. et al., "A comparison of fibrin sealants in relation to their in vitro and in vivo properties", Thrombosis Research, vol. 112, pp. 73-82, (2003).

Luddington, R.J. "Thrombelastography/thromboelastometry", Clin. Lab. Haem., vol. 27, pp. 81-90, (2005).

International Search Report dated Feb. 9, 2009 for PCT application No. PCT/US2008/082225.

Mutch, N.J. et al., "Polyphospates—a novel modulator of Fibrinolysis", Journal of Thrombosis and Haemostasis, vol. 93, No. 4, pp. A21, (2005).

Smith, S.A. et al., "Polyphosphate as a general procoagulant agent", Journal of Thrombosis and Haemostasis, vol. 6, No. 10, pp. 1750-1756, (2008).

Final Office Action for related U.S. Appl. No. 11/816,401, filed Apr. 2, 2008 (dated Aug. 24, 2012), 9 pp.

Final Office Action for related U.S. Appl. No. 12/680,947, filed Jun. 21, 2010 (dated Aug. 23, 2012), 21 pp.

Prosecution history for related U.S. Appl. No. 12/740,762, filed Apr. 30, 2010 (downloaded Sep. 27, 2012), last document dated Sep. 25, 2012, 24 pp.

Mann et al. (2003) "Factor V: a Combination of Dr Jekyll and Mr Hyde," Blood 101(1):20-30.

CA First Office Action, dated Nov. 29, 2012, in Canadian Patent Application No. 2,600,907, a related application, 4 pp.

Church et al. (1988) "Antithrombin Action of Phosvitin and Other Phosphate-Containing Polyanions is Mediated by Heparin Cofactor II," FEBS Letters 237(1,2):26-30.

\* cited by examiner

COAGULATION AND FIBRINOLYTIC CASCADES MODULATOR

REFERENCE TO RELATED APPLICATIONS

This application is a continuation application of co-pending U.S. application Ser. No. 11/362,270, filed Feb. 23, 2006, which claims the benefit of U.S. Provisional Application No. 60/658,776 entitled "COAGULATION AND FIBRINOLYTIC CASCADES MODULATOR" filed 4 Mar. 2005, the entire contents of which are hereby incorporated by reference.

FEDERALLY SPONSORED RESEARCH OR DEVELOPMENT

This application was funded in part under the following research grants and contracts: NIH (NHLBI and NIAID) Grant Nos. P50 HL45402, R01 HL47014, and R01 AI23259. The U.S. Government has certain rights in this invention.

BACKGROUND

A schematic of the clotting cascades is shown in FIG. 15. In the figure the various clotting factors are indicated by their Roman numeral (i.e., factor VII is indicated by VII). The intrinsic cascade (also referred to as the contact pathway of blood coagulation) is initiated when contact is made between blood and certain artificial surfaces. The extrinsic pathway (also referred to as the tissue factor pathway of blood coagulation) is initiated upon vascular injury which leads to exposure of tissue factor (TF) (also identified as factor III). The dotted arrow represents a point of cross-over between the extrinsic and intrinsic pathways. The two pathways converge at the activation of factor X to Xa. Factor Xa has a role in the further activation of factor VII to VIIa. Active factor Xa hydrolyzes and activates prothrombin to thrombin. Thrombin can then activate factors XI, VIII and V furthering the cascade. Ultimately, the role of thrombin is to convert fibrinogen to fibrin, which forms clots.

The fibrinolytic system is responsible for the breakdown of fibrin clots through a series of highly regulated enzymatic reactions. In addition to their role in blood hemostasis, the components of the fibrinolytic system have also been implicated in extracellular matrix degradation and cell migration during inflammation, tumor invasion, tissue repair and angiogenesis (reviewed by [4]). A schematic representation of the proteins and interactions involved in fibrinolysis is shown in FIG. 1. Two main phases are involved: plasminogen activation and subsequent fibrin degradation. Plasminogen activation occurs by the action of either of two serine proteases, tissue-type plasminogen activator (tPA) or urokinase-type plasminogen activator (uPA). The enzymatic activities of these plasminogen activators are opposed by the plasminogen activator inhibitor, PAI-1, a member of the serpin (serine protease inhibitor) superfamily. The product of plasminogen activation is the serine protease, plasmin, whose activity is regulated by another serpin, alpha2-antiplasmin (alpha2-AP). Plasmin proteolytically degrades fibrin into soluble fibrin degradation products (FDPs). Recently, a carboxypeptidase inhibitor of fibrinolysis has been described [5]. This inhibitor serves as a link between coagulation and fibrinolysis, as its main physiological activator is thrombin (especially, thrombin bound to thrombomodulin). For this reason, the molecule is termed Thrombin Activatable Fibrinolysis Inhibitor (TAFI). It should be noted that this inhibitor has also been referred to as carboxypeptidase U, carboxypeptidase R, and plasma carboxypeptidase B, since it was discovered by several groups simultaneously. TAFI circulates as a procarboxypeptidase, which is converted to the active carboxypeptidase enzyme (TAFIa) by limited proteolysis.

Tissue factor pathway inhibitor (TFPI) is one of the physiologically important coagulation inhibitors present in blood. When blood coagulation is initiated, TFPI binds very tightly to the active site of coagulation factor Xa (FXa) and inhibits its enzymatic activity. The inhibited TFPI:FXa complex can then bind to the complex of factor VIIa (FVIIa) and tissue factor (TF), resulting in a fully inhibited tetrameolecular complex (TF:FVIIa:TFPI:FXa). This effectively shuts down further initiation of blood clotting, which is thought to be important in limiting the size of blood clots following injury. In vivo, only a small amount of TFPI circulates in the plasma as free TFPI [24]. (There is another pool of TFPI in plasma that is covalently bound to lipoprotein particles, but it is essentially inactive.) In healthy normal persons, the majority of active TFPI is bound to the endothelial cell surface or is present in platelets [24].

As with other clotting proteins, the plasma levels of TFPI can vary from individual to individual. Normal variation in TFPI levels generally has a limited impact on routine clotting assays for two reasons. First, most normal plasma samples contain fairly low levels of active TFPI (1-20 ng/ml). Second, the influence of natural coagulation inhibitors like TFPI on plasma clotting times is lessened when clotting times are short.

Since routine screening tests for global coagulation function (such as the Prothrombin Time (PT) test) are generally designed to clot very rapidly (the range of normal clotting times in the PT assay is typically 10 to 15 seconds), these tests are only minimally influenced by the normal variation in TFPI levels. However, the influence of TFPI on clotting time in vitro can become significant when the plasma sample contains an unusually high level of TFPI, when other deficiencies in clotting function prolong the clot time and allow TFPI to have a larger influence, or in specialized clotting assays.

Patients with thrombotic episodes are typically treated with anticoagulants. Often, these patients are treated initially with heparin by injection, then gradually switched over to oral anticoagulant therapy (coumadin) for long-term control. The anticoagulant status of patients being treated with coumadin is usually monitored with the PT assay, whose results are used to adjust the coumadin dosage. Multiple studies have described the potential variability of PT results during this period of transition between heparin and coumadin therapy. One possible source of interference in clotting assays in samples from patients undergoing heparin therapy is elevated levels of plasma TFPI. This happens because administration of heparin causes release of the pool of endothelial-bound TFPI into the plasma [25]. In patients with increased TFPI activity, prolonged clot times may be misinterpreted as coagulation factor deficiencies or attributed to the effect of oral anticoagulant (coumadin) therapy.

Some studies have demonstrated that elevated levels of plasma TFPI, especially in patients undergoing heparin therapy, can seriously interfere with the proper interpretation of plasma clotting data. This is especially true for the soluble tissue factor-based clotting assay that is used to measuring plasma factor VIIa levels [26,27]. Thus, the anticoagulant effect of elevated TFPI can prolong the observed clotting times in such clotting assays, yielding a falsely depressed measurement of plasma factor VIIa. Inhibitory anti-TFPI antibodies have been successfully used to eliminate interference from elevated levels of TFPI in such assays [26,27]. However, anti-TFPI antibodies are expensive and must be used at high concentrations to completely block TFPI function, which limits their general usefulness. It would therefore be highly desirable to have a simple and inexpensive method for blocking TFPI anticoagulant function in clotting assays.

The Prothrombin Time (PT) test is widely used to monitor oral anticoagulation therapy by coumarins, as a general screening test for the blood clotting system, and as the basis for specific Factor assays. Clotting times obtained with the PT are primarily dependent on the plasma levels of the vitamin K-dependent coagulation Factors II (prothrombin), VII, and X, and on the levels of two non-vitamin K-dependent proteins, Factor V and fibrinogen. Coumarin treatment antagonizes the vitamin K carboxylase/reductase cycle, thus inhibiting the post-translational conversion of glutamate residues to gamma-carboxyglutamate. Vitamin K-dependent clotting factors contain essential gamma-carboxyglutamate residues in their Gla domains. Patients receiving coumarin therapy will therefore produce undercarboxylated vitamin K-dependent clotting factors with reduced procoagulant activity. This prolongs the PT, chiefly due to depression in the levels of Factors II, VII and X. Successful oral anticoagulant therapy with coumarins requires careful monitoring of the patient's PT in order to achieve an effective level of anticoagulation while minimizing bleeding complications (reviewed by Hirsh et al. [1]).

Polyphosphates have been widely used for many years in a number of commercial applications, including uses in food additives, food processing, and water softeners [1]. Polyphosphates have also been used in dentistry in the treatment of periodontal disease, and polyphosphates have been reported to have antimicrobial activity [1]. Polyphosphates have been used to aid in the refolding of recombinant TFPI [19-21].

Inorganic polyphosphate (polyP) is a ubiquitous polymer formed from phosphate residues linked by high-energy phosphoanhydride bonds. PolyP is found in the environment and has been detected in bacterial, fungal, animal and plant cells, although its presence in human cells has remained less studied [1].

In bacteria as well as in several unicellular eukaryotes, such as trypanosomatid and apicomplexan parasites, the green alga *Chlamydomonas reinhardtii*, and the slime mold *Dictyostelium discoideum*, polyP is accumulated in acidic organelles known as acidocalcisomes where it can reach millimolar or molar levels [2]. It has recently been found that human platelet dense granules are similar to acidocalcisomes in their density, acidity, and ability to accumulate pyrophosphate ($PP_i$), cations, and polyP [3]. This makes acidocalcisomes the only known class of organelles that has been conserved during evolution from bacteria to humans.

SUMMARY

In a first aspect, the present invention is a thromboplastin reagent, comprising (i) TF, (ii) a phospholipid, and (iii) a polyP TFPI blocker.

In a second aspect, the present invention is a composition for promoting clotting, comprising (i) polyP, and (ii) a pharmaceutical carrier.

In a third aspect, the present invention is a method of stopping or slowing bleeding from a wound, comprising contacting blood from the wound with polyP.

In a fourth aspect, the present invention is a method of blocking TFPI, comprising including polyP in a composition comprising the TFPI.

In a fifth aspect, the present invention is a reagent for a clotting assay, comprising an activator of clotting, and polyP.

DEFINITIONS

V or factor V means coagulation factor V.
Va or factor Va means coagulation factor Va.
VII or factor VII means coagulation factor VII.
VIIa or factor VIIa means coagulation factor VIIa.
X or factor X means coagulation factor X.
Xa or factor Xa means coagulation factor Xa.
VIII or factor VIII means coagulation factor VIII.
VIIIa or factor VIIIa means coagulation factor VIIIa.
IX or factor IX means coagulation factor IX.
IXa or factor IXa means coagulation factor IXa.
XI or factor XI means coagulation factor XI.
XIa or factor XIa means coagulation factor XIa.
XII or factor XII means coagulation factor XII.
XIIa or factor XIIa means coagulation factor XIIa.
tPA means tissue-type plasminogen activator.
uPA means urokinase-type plasminogen activator.
TAFI means thrombin-activatable fibrinolysis inhibitor (procarboxypeptidase), also known as procarboxypeptidase B, U, or R.
TAFIa means the activated form of TAFI (active carboxypeptidase).
TFPI means tissue factor pathway inhibitor.
PolyP$_n$ means a compound of the following formula:

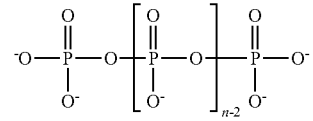

where the value of n is equal to the number of $PO_3$ units in the molecule, and n is at least 3. Polyphosphate (polyP) is a generic term for polyP$_n$, including mixtures, where n of each polyP$_n$ is at least 3. Concentrations of polyphosphate and any polyP$_n$ may be expressed as "phosphate equivalents", which means the concentration of $PO_3$ moieties (for example, 1 µM polyP$_{75}$ is the same as 75 µM phosphate equivalents of polyP$_{75}$).

A polyP TFPI blocker is one or more polyphosphates which block the activity of TFPI, as determined by the TFPI blocking test. The TFPI blocking test is a set of PT clotting assays, comparing clotting times using thromboplastin reagents with and without the polyP TFPI blocker added, and with and without TFPI added to the pooled plasma. PT clotting assays are performed in a coagulometer (such as a STart coagulometer, Diagnostica Stago, Parsippany N.J.) by pre-incubating 50 µl of human plasma with 50 µl of the thromboplastin reagent at 37° C. for 120 sec. Clotting is then initiated by adding 50 µl of 25 mM calcium chloride solution that has been pre-warmed to 37° C. The time to clot formation is then measured relative to the point of addition of calcium chloride. TFPI is added to the plasma at a concentration of 50 ng/ml immediately before use. The polyphosphate to be tested is added to the clotting reagent at a concentration 75 µM phosphate equivalents. The thromboplastin reagent contributes one-third of the total volume in the clotting reaction, and therefore the final concentration of the polyphosphate is one-third of its concentration in the thromboplastin reagent.

FVII means any protein that exhibits Factor VII clotting activity of human Factor VII. The Factor VII clotting activity of a protein is determined by comparing the amount of the protein necessary to give the same clotting time as human Factor VII in the following assay: 50 μL of citrated Factor VII deficient plasma, together with human Factor VII or the protein, is incubated in a cuvette for 2 min at 37° C., after which clotting is initiated by adding 100 μL pre-warmed calcium-containing thromboplastin reagent, and the time to clot formation is measured with a coagulometer, such as an ST4 coagulometer (Diagnostica Stago, Parsippany, N.J.). The amount of human Factor VII and the type of thromboplastin reagent are preferably selected to give a clotting time of 10-15 seconds. The molar amount of human Factor VII that achieves a given clotting time is divided by the molar amount of the protein that gives the same clotting time, which gives the relative Factor VII clotting activity of the protein. Preferably, FVII has at least 1% of the clotting activity of human Factor VII. FVII includes, for example, natural human Factor VII, natural human Factor VIIa, recombinant human Factor VII [22] and VIIa, and other mammalian Factor VII and VIIa (such as natural rabbit Factor VII and natural rabbit Factor VIIa).

"Factor VIIa equivalents" means that the amount of FVII present has the same clotting activity as the specified amount of natural human Factor VIIa. For example, "10 ng Factor VIIa equivalents of FVII" means that the amount of FVII present has the same clotting activity as 10 ng of natural human Factor VIIa.

rTF means any recombinant tissue factor which is not identical to natural mammalian tissue factor. This includes recombinant tissue factor produced in bacteria (which differs from natural mammalian tissue factor in molecular weight since it does not have attached carbohydrate), and recombinant tissue factor produced in insect cells (baculovirus) (which differs from natural mammalian tissue factor in molecular weight, since certain problematic domains have been removed).

TF means any tissue factor protein, such as rTF and natural mammalian tissue factors.

Thromboplastin reagent is any reagent which contains TF and that when 50 μL of the reagent is mixed with 50 μL plasma pooled from normal individuals and incubated for 120 sec at 37° C., then 50 μL pre-warmed 25 mM $CaCl_2$ solution is added, will result in clotting within 1 minute. Optionally, the thromboplastin reagent may contain calcium ion, in which case no $CaCl_2$ solution is added.

Dilute PT assay is a PT assay performed using a thromboplastin reagent that has been diluted with a suitable buffer (dilute thromboplastin) to yield prolonged clotting times in a PT assay.

Synthetic thromboplastin reagent is any thromboplastin reagent that contains rTF. Alternatively, synthetic thromboplastin reagent contains TF and does not contain any actin, hexokinase, and alkaline phosphatase.

"Prothrombin time ratio" (PTR) for a "1% Factor" of a thromboplastin reagent is determined by dividing the PT for a plasma containing 1% of the normal level of the specified factor by the PT for pooled normal plasma (100% factor) obtained with the thromboplastin reagent. For example, the "prothrombin time ratio for 1% Factor VII" of a thromboplastin reagent is determined by dividing the PT for a plasma containing 1% of the normal level of Factor VII by the PT for pooled normal plasma (100% factor) obtained with the thromboplastin reagent.

BRIEF DESCRIPTION OF THE DRAWINGS

FIG. 2a: Pooled normal plasma was supplemented with 1.4 nM uPA and clotting was initiated by adding calcium chloride; half-maximal absorbance (light scattering), indicative of clot formation, was reached by 25 min and the time to 50% clot lysis was 43 min. FIG. 2b: Plasma clot/lysis reaction as in FIG. 2a, but with the addition of 75 μM phosphate equivalents of $polyP_{75}$. Results in both panels are the mean of duplicate wells. These data are a representative example of 10 experiments.

FIG. 6a: Pooled normal plasma was supplemented with 1.4 nM uPA and clotting was initiated by adding a mixture of calcium chloride and thrombin. Clot lysis was complete by about 50 min in the absence of polyP (open circles), but clot lysis was severely attenuated in the presence of 75 μM phosphate equivalents of $polyP_{75}$ (filled circles). Addition of 6.25 μM CPI accelerated clot lysis equally well in the absence (open triangles) and the presence of $polyP_{75}$ (filled triangles). FIG. 6b: TAFI-deficient plasma was supplemented with 1.4 nM uPA and clotting was initiated by adding a mixture of calcium chloride and thrombin. Rapid clot lysis was observed under all conditions tested: uPA only (open circles); 75 μM phosphate equivalents of $polyP_{75}$ but no CPI (filled circles); 6.25 μM CPI but no polyP (open triangles); and 75 μM phosphate equivalents of $polyP_{75}$ plus 6.25 μM CPI (filled triangles). Results in both panels are the mean of duplicate wells. These data are a representative example of 5 experiments.

FIG. 7a: the effect of polyP$_{75}$ on clotting of pooled normal plasma. Normal plasma was incubated in the well of a polystyrene 96-well plate for 2 min at ambient temperature in the absence (open circles) or presence (filled circles) of 75 µM phosphate equivalents of polyP$_{75}$. Clotting was then induced by addition of calcium chloride and absorbance at 405 nM was measured at 37° C., timed from addition of calcium chloride. FIG. 7b: the effect of polyP$_{75}$ on clotting of factor XII-deficient plasma. Clotting reactions were carried out as in FIG. 7a, except that factor XII-deficient plasma was employed in place of pooled normal plasma. The times to clot formation (>10 min) were significantly longer than with pooled normal plasma, both in the absence of polyP (open triangles) and in the presence of polyP$_{75}$ (filled triangles). FIG. 7c: order of addition affects the ability of polyP$_{75}$ to stimulate clotting. Clotting reactions were performed as in FIG. 7a, except that the initial 2 min incubation of plasma with polyP$_{75}$ at ambient temperature was performed with a 40 µl aliquot of either factor XII-deficient or normal plasma. At the end of the 2 min incubation period, a second 40 µl aliquot of plasma was added, immediately after which clotting was initiated with calcium chloride. When the first incubation was with normal plasma, the second aliquot was with factor XII-deficient plasma, and vice versa. When factor XII-deficient plasma was pre-incubated with polyP$_{75}$ for 2 min and then normal plasma was added, clot times were longer than 10 min (filled triangles). When normal plasma was pre-incubated with polyP$_{75}$ for 2 min and then factor XII-deficient plasma was added, clot times were less than 5 min (filled circles). Results in all three panels are the mean of duplicate wells. These data are a representative example of 3 experiments.

DETAILED DESCRIPTION

Figure 1:
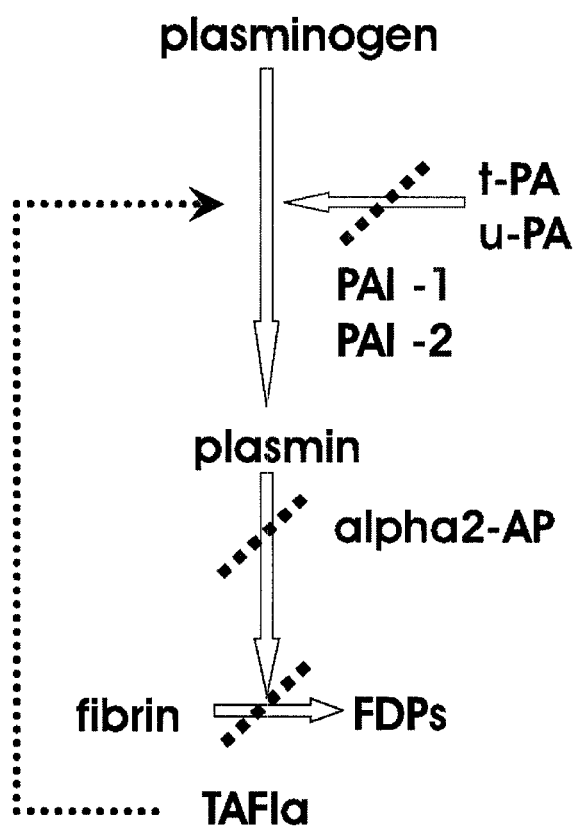
FIG. 1 illustrates the fibrinolytic cascade.

Platelets exert strongly procoagulant and antifibrinolytic effects. The anticoagulant effect of platelets has been attributed to the presence of the inhibitors PAI-1 and alpha2-antiplasmin in platelet alpha granules. Many lines of evidence suggest that the strongly antifibrinolytic nature of platelets cannot solely be explained by the presence of these inhibitors, however. Recently, polyP was discovered at high concentration in dense granules of human platelets [3]. PolyP in platelet dense granules has a chain length of 70-75 phosphate units and is present in millimolar phosphate equivalent levels. It is released from platelets upon thrombin stimulation together with serotonin and PP$_i$[3]. This discovery prompted us to hypothesize that release of polyP from activated platelets may serve to regulate blood coagulation and/or fibrinolysis.

The present invention makes use of the discovery that polyP can promote coagulation through both the extrinsic and intrinsic pathways, and also inhibit fibrinolysis. PolyP may be used in compositions to promote clotting, through either or both the extrinsic and intrinsic pathways. Furthermore, addition of polyP to thromboplastin reagents or other clotting reagents may be used to block the effects of TFPI, improving the accuracy of clotting test for patients in the transition from heparin therapy and other anticoagulant therapies.

PolyP contains at least 3 PO$_3$ moieties. For blocking TFPI and promoting clotting, polyP may be used. Preferably, polyP$_n$ with n of at least 25 may be used, for example n=25-1000, more preferably, n=25-100. For inhibiting fibrinolysis, polyP$_n$ with n greater than 25 is preferred, for example n=26-1000 (including 27, 28, 29, 30, 31, 32, 33, 34, 35, 36, 37, 38, 39, 40, 41, 42, 43 and 44), more preferably n is at least 45, including 45-1000. For promoting clotting via the intrinsic pathway, polyP$_n$ with n greater than 25 is preferred, for example n=26-1000 (including 27, 28, 29, 30, 31, 32, 33, 34, 35, 36, 37, 38, 39, 40, 41, 42, 43 and 44), more preferably n is at least 45, including 45-1000.

In a composition for promoting clotting, the concentration of polyP is preferably at least 1 nM phosphate equivalents, such as 1 nM to 100 mM, more preferably at least 100 nM phosphate equivalents, such as 100 nM to 10 mM, most preferably 7500 nM to 10 mM phosphate equivalents. For compositions to promote clotting which are internalized into a patient, preferably the maximum amount of polyP used in a single dose is 10 μmol phosphate equivalents per kg body weight. If administered intravenously, preferably the maximum amount of polyP used in a single dose will result in a plasma concentration in the patient of 75 to 225 μM phosphate equivalents.

Preferably, the polyP is used together with a phosphatase inhibitor, to slow down the breakdown of polyP.

The polyphosphates to promote clotting and/or prevent fibrinolysis may be administered through oral (such as mouthwashes, tablets and lozenges), parenteral, topical, nasal, aural, rectal (such as suppositories and enemas), etc., routes in the treatment of bleeding. Therapeutic compositions may be formed, to stop bleeding from a wound, by contacting blood from the wound, or by contacting the wound with the composition. The composition may contain the components needed to initiate the intrinsic pathway, the extrinsic pathway, inhibit fibrinolysis, or any combination thereof. The therapeutic composition may be in a variety of forms, depending on the location of the wound: a topical composition, a nasal spray, a suppository, a mouthwash, an injectable composition, or carried in or on a bandage or a wound dressing. Therapeutic compositions are preferably sterile, and may contain preservatives. Therapeutic compositions may be administered in a wide variety of forms including unit dosage forms (tablets, capsules, pre-measured ampoules, pre-measured powder pouches, or any other therapeutic composition intended for a single administration), and may be combined with various pharmaceutical carriers. Such carriers include solid diluents or fillers, sterile aqueous media and various non-toxic organic solvents. As used herein, pharmaceutical carriers includes solid substrates, such as fibers and fabrics used in bandages, wound dressings, and tampons. When suspensions, emulsions or solutions are desired, the polyphosphate may be combined with various sweetening or flavoring agents (for oral administration), coloring matter or dyes, and emulsifying and/or suspending agents as well, together with such diluents as water, ethanol, propylene glycol, glycerin and combinations thereof.

A nasal spray may contain the composition in wet or dry powder form. In wet form, the composition may contain the same additives as those described below for injectable compositions. As a dry powder, in may also included other customary additives and/or carriers, such as those described in U.S. Pat. No. 6,815,424.

A mouthwash will contain the composition in wet form, optionally contain other ingredients common to a mouthwash. Examples include those described in U.S. Pat. Nos. 5,945,087 and 5,338,538. These compositions may be used to rinse the mouth, such as by gargling, particularly by hemophiliacs after dental work.

For oral administration in dry form, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are useful for tabletting purposes. Solid compositions of a similar type may also be employed as fillers in gelatin capsules.

For administration by injection, polyphosphates in, for example, water, saline, sesame or peanut oil, aqueous propylene glycol, or another pharmaceutical carrier, are suitable. Aqueous solutions should be suitably buffered, if necessary and the liquid diluent preferably first rendered isotonic. The aqueous solutions are suitable for intravenous injection purposes. The oily solutions are suitable for parenteral, intramuscular and subcutaneous injection purposes. Injection into various body cavities may be used to promote clotting for wounds bleeding into a body cavity.

Bandage and wound dressings may contain the composition in wet or dry form. These may be prepared by applying a solution or suspension of polyP, such as those described above for injection together with any other additives desired, to a bandage or wound dressing, and drying the solution or suspension. The solution or suspension preferably contains the polyP in the concentrations noted above. Powdered polyP may also be impregnated into the bandage or dressing, or woven into the fibers used to form the bandage or dressing.

A topical composition may be in wet or dry powder form, and may include a topically acceptable carrier, as well as a pharmaceutical carrier. Examples of such topically acceptable carriers may be found in International Patent Publication WO 00/62742, published Oct. 26, 2000; U.S. Pat. Nos. 5,691,380; 5,968,528; 4,139,619; and 4,684,635; as well as the CTFA Cosmetic Ingredient Handbook, Second Edition (1992). Suitable topically acceptable carriers, as well as other pharmaceutical carriers, are also described in Remington's Pharmaceutical Sciences, 17th ed., Mack Publishing Company, Easton, Pa. (1990), which is a standard reference text in this field. A topically applied composition of the invention may be in a form suitable for topical application, such as an emulsion (including oil-in-water, water-in-oil, water-in-oil-in-water, and oil-in-water-in-silicone emulsions), a cream, an ointment, an aqueous solution, a lotion or an aerosol.

PolyP may be used in any clotting assay, to block TFPI, or as an activator of clotting. A reagent for a clotting assay, which contains an activator of clotting and optionally buffer and/or $Ca^{2+}$ (for example, adding $CaCl_2$), may also contain polyP to block TFPI that may be present in the sample from a patient. Alternatively, polyP may be used as the activator of clotting, in addition to, or as a substitute for, the activator of clotting typically used in that reagent. The following table is a list of clotting assays and their associated activators of clotting present in the reagent for that clotting assay [28]:

TABLE

Clotting assays and reagents for clotting assays.

| Assay | Name of reagent for clotting assay (if any) | Activator of clotting | Optional ingredients in reagent |
|---|---|---|---|
| Prothrombin Time | Thromboplastin | Tissue factor | Phospholipids, buffer, calcium |
| Activated Partial Thromboplastin Time | Partial thromboplastin | Kaolin or silica | Phospholipids, buffer, calcium |
| Partial Thromboplastin Time | Partial thromboplastin | Phospholipids | Buffer, calcium |
| Xa Clot Time | | Factor Xa | Phospholipids, buffer, calcium |
| Thrombin Clot Time | | Thrombin | Buffer, calcium |
| Venom based clot | | Snake venom or | Phospholipids, |

TABLE-continued

Clotting assays and reagents for clotting assays.

| Assay | Name of reagent for clotting assay (if any) | Activator of clotting | Optional ingredients in reagent |
|---|---|---|---|
| time (such as Russell's Viper Venom Time) | | purified snake venom protein | buffer, calcium |
| VIIa Clotting Assay | | Soluble tissue factor | Phospholipids, buffer, calcium |

When used in a thromboplastin reagent to block TFPI, the concentration of polyP present is preferably at least 300 nM phosphate equivalents, such as 300 nM to 500 µM, more preferably at least 7500 nM phosphate equivalents, such as 7500 nM to 500 µM.

Preferably, the thromboplastin reagent contains $Ca^{2+}$, or the $Ca^{2+}$ may be added just prior to use of the reagent. The $Ca^{2+}$ may be provided with the thromboplastin reagent in a kit, with each part separately packed, optional with each reagent is dry form. $Ca^{2+}$ is preferably added as $CaCl_2$. The amount of $Ca^{2+}$ is preferably 1-100 mM, more preferably 5-75 mM, more preferably 10-50 mM, including 10 mM, 12.5 mM, 15 mM, 20 mM, 25 mM, 30 mM, 35 mM, 40 mM and 45 mM.

Ionic strength may be adjusted by adding salts, such as alkali metal and alkaline earth metal salts, including halides, sulfates, nitrates and acetates, such as NaCl and KCl. Preferably, the salts are present in an amount of 0-200 mM, 10-150 mM, 15-125 mM, or more preferably 25-100 mM.

The thromboplastin reagents contain TF relipidated into phospholipids, such as phosphatidylcholine (PC), phosphatidylserine (PS) and phosphatidylethanolamine (PE). At least a portion of the phospholipids are net negatively charged phospholipids, such as PS, phosphatidylglycerol (PG), phosphatidic acid (PA), or phosphatidylinositol (PI). Preferably, the amount of PS is from 5-50%, more preferably from 10-40%, including 15%, 20%, 25%, 30%, and 35%, of the total phospholipids content. The amount of PE is preferably 0-50%, more preferably 5-40%, including 10%, 15%, 20%, 25%, 30%, and 35%, of the total phospholipids content. Preferably, the remainder of the phospholipids content is composed of neutral phospholipids, such as PC, for example 0-95%, more preferably 40-90%, including 45%, 50%, 55%, 60%, 65%, 70%, 75%, 80%, and 85%, of the total phospholipid content. The TF may be natural TF which has been extracted from tissue, or rTF. The thromboplastin reagent may also be of the type described in U.S. provisional patent application "UNIVERSAL PROCOAGULANT" to James H. Morrissey and Emily M. Kerestes, filed 16 Feb. 2005, attorney docket no. ILL05-060-PRO, application Ser. No._____, the entire contents of which are hereby incorporated by reference.

The International Sensitivity Index (ISI) value of the thromboplastin reagent is preferably 0.6 to 2, more preferably 0.8 to 1.5, even more preferably 0.8 to 1.2, and most preferably 0.9 to 1.1. Alternatively, preferably the ISI value of the thromboplastin reagent is at most 1.5 or at most 1.2. ISI value of the thromboplastin reagent should be determined by the WHO approved method [23].

Preferably, the PTR for 1% Factor VII is 1-10, more preferably 1-5, even more preferably 1-2, and most preferably at most 1.5, including at most 1.4, 1.3, 1.2 and 1.1.

Preferably, the PTR for 1% Factor II (prothrombin) is 1-10, more preferably 1.5-7, even more preferably 2-7, and most preferably at least 2, including at least 3, 4, 5 and 6.

Preferably, the PTR for 1% Factor X is 1-10, including 1.1, 1.2, 1.3, 1.4, 1.5, 1.6, 1.7, 1.8, 1.9, 2, 3, 4, 5, 6 and 7.

Preferably, the PTR for 1% Factor VII is at most 2 and the PTR for 1% Factor II is at least 4; more preferably the PTR for 1% Factor VII is at most 1.5 and the PTR for 1% Factor II is at least 5; and most preferably the PTR for 1% Factor VII is at most 1.2 and the PTR for 1% Factor II is at least 6.

The thromboplastin reagents may be provided in dried form, by freeze-drying, spray-drying, or other suitable protein drying methods. The reagents may be dried onto strips or other solid supports, and may be provided as kits with the components provided separately packaged, or groups of the components packaged into 2 or more packages. Some or all of the components may be provided in dried forms, and other components provided in saline or a physiological buffer. A thromboplastin reagent provided as a kit may contain the thromboplastin reagent(s) in one or more containers, and the polyP supplied in a separate contain, so that it may be added only when necessary.

Thromboplastin reagents of the present invention may contain added FVII.

Addition of minute amounts of Factor VIIa to the thromboplastin reagent can be used to minimize sensitivity to Factor VII and to further manipulate responses to other factors. This is more fully explained in "THROMBOPLASTIN REAGENTS" U.S. patent application Ser. No. 10/931,282 to Morrissey et al., filed on Aug. 31, 2004. Any FVII may be used including any mammalian Factor VII or VIIa (such as human, rabbit, rat, cow, etc.). Preferably the thromboplastin reagents contain added Factor VIIa, more preferably human Factor VIIa. The FVII may be prepared recombinantly [22].

Preferably, the amount of FVII present is less than the amount of Factor VII or Factor VIIa found in the plasma of normal individuals, including the amount of Factor VII or VIIa found in Factor II- and Factor X-deficient plasmas. The amount of FVII present is preferably 0.1 to 10 nanograms/milliliter (ng/ml) Factor VIIa equivalents, 1 to 6 ng/ml Factor VIIa equivalents, or 2.5 to 5 ng/ml Factor VIIa equivalents, and more preferably at least 1 ng/ml or at least 2.5 ng/ml Factor VIIa equivalents. Alternatively, the amount of FVII may be expressed in picomolar (pM) amounts; such as 1-1000 pM Factor VIIa equivalents, 50-400 pM Factor VIIa equivalents, preferably at least 150 pM Factor VIIa equivalents or at least 200 pM Factor VIIa equivalents.

Thromboplastin reagents may be used to monitor any anticoagulant drug therapy. Table 1 below lists a variety of these drugs.

TABLE 1

Anticoagulant drugs that may be monitored with thromboplastin reagents

| | |
|---|---|
| Coumarin Derivatives (block production of functional factors II, VII, and X): | Warfarin (COUMADIN ®)[1] Nicoumalone (ACENOCOUMAROL ™)[1] Dicoumarol (BISHYDROXYCOUMARIN ™) Phenprocoumon |
| Thrombin (FIIa) Inhibitors | Argatroban (NOVASTAN ®)[1] Ximelgatran (EXANTA ®)[2] BIBR 1048[2] BIBR 953 Desirudin (REVASC ®)[1] Lepirudin (REFLUDAN ® or PHARMION ®)[1]Bivalirudin (ANGIOMAX ®, previously HIRULOG ®)[1] |

TABLE 1-continued

Anticoagulant drugs that may be monitored with thromboplastin reagents

| | |
|---|---|
| FXa Inhibitors | DX-9065a[2] |
| | DPC 906[2] |
| | Antistasin[3] |
| TF/FVIIa Inhibitors | Anti-TF antibodies |
| | Recombinant Nematode Anticoagulant Protein (rNAPc2)[2] |
| | Recombinat Tissue Factor Pathway Inhibitor (TIFACOGIN ™)[2] |
| | FVIIai[3] |
| ART-123 ™ (recombinant soluble thrombomodulin)[2] | |

[1]FDA approved for use in humans
[2]Evaluated in clinical trials but not yet approved
[3]Still in development (animal studies only)

EXAMPLES

PolyP Affects Both the Rate of Plasma Clotting and the Rate of Fibrinolysis

Figure 2:
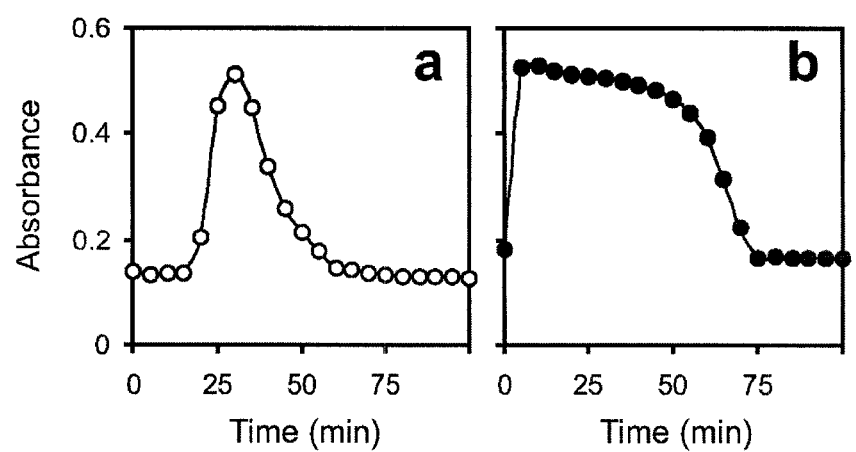
FIGS. 2a and 2b are graphs showing that polyP accelerates plasma clotting and delays fibrinolysis.

The role of polyP in blood coagulation and fibrinolysis was initially investigated using a combined model of plasma clotting and lysis. In this system, clotting of citrated, pooled normal human plasma is initiated by adding calcium chloride. Clotting initiated in this way occurs through the intrinsic pathway of blood coagulation and is relatively slow in the absence of an added contact activator. Thrombin (the final enzyme in the clotting cascade) proteolytically converts fibrinogen to fibrin, which spontaneously polymerizes to form a fibrin gel, or clot. Clotting of fibrin is associated with an increase in turbidity of the plasma, which is easily monitored by measuring the change in absorbance of light at 405 nm. Addition of a plasminogen activator to the plasma at the same time as the calcium ions allows the activation of plasminogen to plasmin, and subsequent lysis of the fibrin clot. Lysis is observed as a decrease in turbidity over time. As seen in FIG. 2a, the plasma clotted following calcium addition, reaching half-maximal absorbance at approximately 25 min. In the presence of uPA the clot dissolved, with 50% clot lysis occurring at 43 min. (In the absence of uPA, the clot formation phase was identical to that described but no lysis occurred; data not shown.)

Adding polyP with a chain length of 75 phosphate units (polyP$_{75}$) to plasma in this model dramatically affected both the rate of plasma clotting and the rate of fibrinolysis. The time to reach half maximal absorbance was shortened to less than 5 min in the presence of polyP$_{75}$ (FIG. 2b), compared to approximately 25 min in the absence of polyP (FIG. 2a). In addition, the presence of polyP$_{75}$ increased the time to 50% lysis to 68 min (FIG. 2b), compared to 43 min with uPA alone (FIG. 2a). These results indicate that polyP both accelerates clotting and inhibits fibrinolysis.

PolyP Inhibits Fibrinolysis

Figure 3:
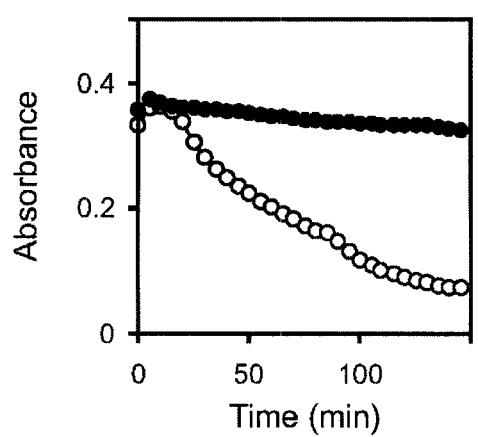
FIG. 3 is a graph showing that polyP inhibits fibrinolysis. Pooled normal plasma was supplemented with 1.4 nM uPA and clotting was initiated by adding a mixture of calcium chloride and thrombin. In the absence of polyP (open symbols), plasma clotted rapidly and then lysed over the next 100 min. In the presence of 75 μM phosphate equivalents of $polyP_{75}$ (closed symbols), plasma also clotted rapidly but failed to lyse over the next 150 min. Results are the mean of duplicate wells. These data are a representative example of 10 experiments.

In order to study the effect of polyP on fibrinolysis independent of its effect on clotting times, the model was modified such that clotting was initiated by a mixture of calcium ions and thrombin in the presence of uPA (pooled normal plasma supplemented with 1.4 nM uPA). The amount of thrombin was chosen to yield rapid clotting times, permitting analyses to focus on the lytic phase only. As seen in FIG. 3, thrombin rapidly induced plasma clotting in the presence or absence of polyP$_{75}$, such that clotting was nearly complete by the first time point. In the absence of polyP, the clots subsequently lysed, with a 50% lysis time of 61 min in this experiment. In the presence of polyP$_{75}$, clot lysis was strongly inhibited (i.e., time to 50% lysis exceeded 150 min). Similar effects were also observed when tPA was substituted for uPA in this clot lysis model: lysis was abrogated by the presence of polyP$_{75}$ (data not shown). The magnitude of the effect of polyP$_{75}$ on the inhibition of fibrinolysis was dependent on the uPA concentration. At high uPA concentrations the effect of polyP$_{75}$ could be masked, presumably reflecting a balance situation between uPA and polyP within the clot (data not shown).

Figure 4:
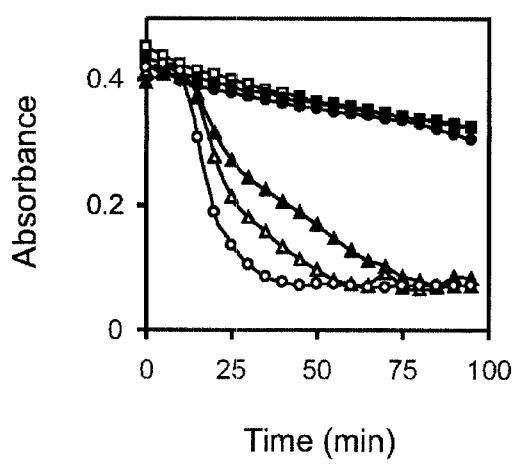
FIG. 4 is a graph showing that inhibition of fibrinolysis by polyP is concentration-dependent. Pooled normal plasma was supplemented with 1.4 nM uPA and clotting was initiated by adding a mixture of calcium chloride and thrombin. $PolyP_{75}$ was included at the following concentrations: 0 nM phosphate equivalents (open circles); 750 nM phosphate equivalents (open triangles); 3750 nM phosphate equivalents (filled triangles); 7.5 μM phosphate equivalents (open squares); 37.5 μM phosphate equivalents (filled squares); and 75 μM phosphate equivalents (filled circles). Results are the mean of duplicate wells. These data are a representative example of 3 experiments.
Figure 5:
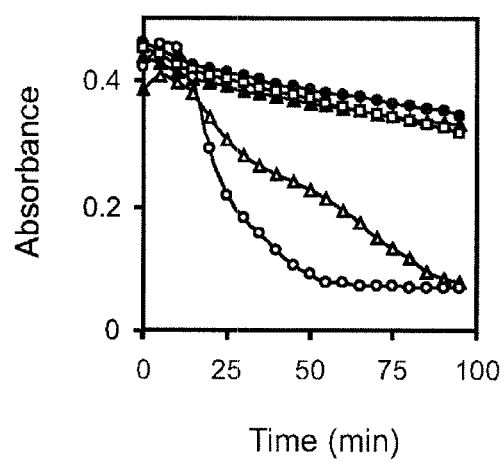
FIG. 5 is a graph showing that the antifibrinolytic effect of polyP depends upon chain length. Pooled normal plasma was supplemented with 1.4 nM uPA and clotting was initiated by adding a mixture of calcium chloride and thrombin (open circles: no polyP). PolyP of different chain lengths was included at 75 μM phosphate equivalents: $polyP_{25}$ (open triangles); $polyP_{45}$ (filled triangles); $polyP_{65}$ (open squares) and $polyP_{75}$ (filled circles). Results are the mean of duplicate wells. These data are a representative example of 3 experiments.

The inhibition of fibrinolysis by polyP$_{75}$ was concentration-dependent, with an optimal concentration range of 100 nM to 1 μM polyP$_{75}$ (FIG. 4). The polyP chain length was also important. PolyP$_{45}$, polyP$_{65}$ and polyP$_{75}$ had comparable abilities to inhibit fibrinolysis, while PolyP$_{25}$ had reduced ability to inhibit fibrinolysis (FIG. 5). Very short phosphate molecules, such as sodium phosphate ($P_i$), $PP_i$, or sodium tripolyphosphate (polyP$_3$) had no discernable effect on fibrinolysis (data not shown). It should be noted that the highest polyP concentrations used (equivalent to 75 μM phosphate monomer) are far below the mM concentrations of calcium ions employed in our assays. This rules out the possibility that polyP influences coagulation or fibrinolysis simply by reducing the free calcium ion concentration (e.g., by forming complexes with calcium ions or by precipitating them).

There are a number of potential mechanisms by which polyP could inhibit fibrinolysis. For example, polyP could attenuate plasminogen activation by inhibiting tPA or uPA enzymatic activity. Alternatively, polyP could act by enhancing the activation or function of one of the plasma inhibitors of fibrinolysis. The direct effect of polyP$_{75}$ on uPA or tPA enzymatic activity was tested in enzymatic assays using purified proteins, and polyP$_{75}$ was found not to inhibit either enzyme (data not shown).

Inhibition of Fibrinolysis by PolyP is Dependent Upon Thrombin Activatable Fibrinolysis Inhibitor (TAFI)

One possible target of polyP is the plasma fibrinolysis inhibitor, TAFI. The mechanism of action of TAFIa differs from classical (serpin) inhibitors. This is because it decreases the rate of fibrinolysis, not by direct interaction with active enzymes, but by removing C-terminal lysine and arginine residues from fibrin. C-terminal lysine residues, which are exposed on partially degraded fibrin, bind plasminogen and tPA. This binding serves to localize plasminogen and tPA enzymes at their site of action, providing a positive feedback mechanism whereby conversion of plasminogen to plasmin is accelerated. Thus, TAFIa negatively modulates this feedback response by eliminating the residues important in binding of tPA and plasminogen [6-8]. The concentration of TAFI in plasma is approximately 100 nM, but only a small amount of TAFIa is required to dramatically prolong lysis. A half-maximal effect of TAFIa on lysis is seen at 1 nM, with maximal effect at 10 nM [9].

No known physiological inhibitor of TAFIa exists. Its activity is believed to be regulated by its extremely thermolabile nature, with a half-life of approximately 10 min at 37° C. Many naturally occurring variations in TAFI exist, some of which confer stability and profoundly change the antifibrinolytic potential in vivo [9,10]. The spontaneous decay of TAFIa is a result of an induced conformational change rather than proteolytic cleavage [11].

Figure 6:
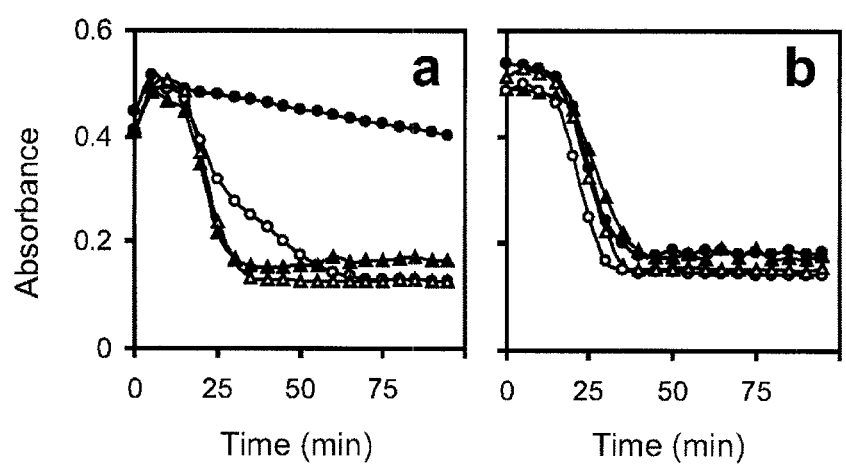
FIGS. 6a and 6b are graphs showing that attenuation of fibrinolysis by polyP is TAFI-dependent.

The role of TAFI in the polyP-dependent delay of clot lysis was investigated. This question was first examined using a specific inhibitor of TAFIa in plasma, the carboxypeptidase inhibitor derived from potato tubers (CPI). Pooled normal plasma was clotted by adding calcium ions and thrombin in the presence or absence of CPI (6.25 μM) and/or polyP$_{75}$ (75 μM phosphate equivalents). As was observed in previous experiments, clot lysis was dramatically inhibited in the presence of polyP$_{75}$ (FIG. 6a). When CPI was added to the plasma (to eliminate any contribution from TAFIa), the rate of fibrinolysis was increased. Interestingly, polyP$_{75}$ no longer had any effect on the rate or extent of fibrinolysis when CPI was present (FIG. 6a). This indicates that the ability of polyP$_{75}$ to delay fibrinolysis is dependent upon plasma TAFI. To confirm this observation, the role of TAFI in the prolongation of fibrinolysis by polyP$_{75}$ was examined using plasma immunodepleted of TAFI. Again, in stark contrast to its effect on normal plasma, addition of polyP$_{75}$ to TAFI-deficient plasma had no effect on clot lysis time (FIG. 6b).

PolyP Accelerates the Contact Pathway of Blood Coagulation

Figure 7:
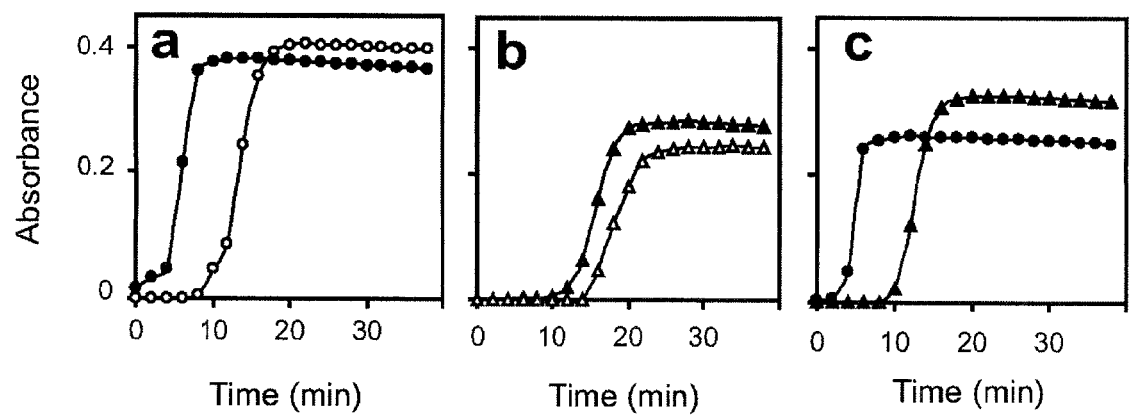
FIGS. 7a, 7b and 7c are graphs showing that activation of coagulation factor XII by the contact pathway is enhanced by polyP.

The effect of polyP on plasma coagulation was evaluated further, using a plasma clotting assay in multiwell plates carried out in the absence of any added plasminogen activator. Clotting of plasma in such assays is dependent upon the contact pathway of blood coagulation, and since the assays are conducted in plastic (polystyrene) wells with no other contact activator added, clotting times are slow. The time to clot formation was more than 10 min in the absence of polyP, but was shortened to about 5 min by the inclusion of polyP$_{75}$ (FIG. 7a). To directly test the idea that polyP acts through the contact pathway, these clotting assays were repeated using factor XII-deficient plasma, resulting in greatly prolonged clotting times (nearly 20 min; FIG. 7b). Adding polyP$_{75}$ to factor XII-deficient plasma resulted in clotting times that were still greatly prolonged (FIG. 7b), compared with normal pooled plasma (FIG. 7a).

The initiation phase of the contact pathway of blood clotting is not calcium-dependent, so factor XII activation can take place in citrated plasma without added calcium ions. When pooled normal plasma was pre-incubated for 2 min with polyP$_{75}$ and then calcium chloride added, clotting times were significantly shortened relative to those of plasmas not pre-incubated with polyP (data not shown). This suggested that polyP$_{75}$ might accelerate the initiation phase of the contact pathway. Indeed, many of the known artificial activators of the contact pathway contain negatively charged surfaces or negatively charged polymers [13]. Accordingly, the hypothesis that polyP might serve to activate the contact phase of clotting was tested by pre-incubating either pooled normal plasma or factor XII-deficient plasma with polyP$_{75}$ for 2 min. After this pre-incubation period, a second aliquot of plasma (either factor XII-deficient plasma or normal plasma, respectively) was added, followed immediately by calcium chloride, and the time to clot formation was measured. Thus, the clotting assays in this experiment contained a 50:50 mixture of normal and factor XII-deficient plasma, although the order in which the plasmas were pre-incubated with polyP$_{75}$ differed. Pre-incubation of polyP$_{75}$ with normal plasma resulted in significant shortening of the clotting time (to approximately 4 min; FIG. 7c). On the other hand, pre-incubation of polyP$_{75}$ with factor XII-deficient plasma resulted in long clotting times (>10 min), in spite of the fact that 50% of the plasma volume was contributed by pooled normal plasma (FIG. 7c). These results demonstrate that pre-incubation of plasma with polyP$_{75}$ shortens the clotting time in a factor XII-dependent manner, indicative of activation of the contact pathway of blood clotting.

Figure 8:
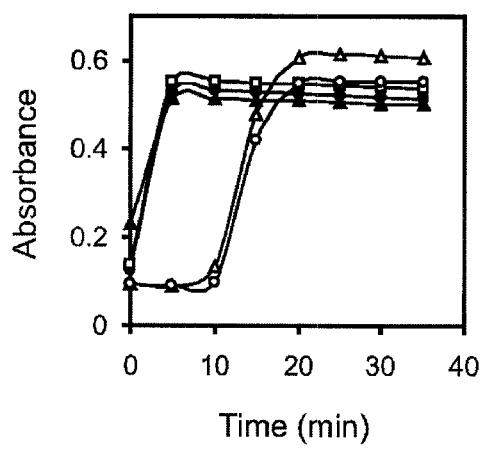
FIG. 8 is a graph showing that polyP polymers of greater than 25-phosphates are required to enhance factor XII activation. Pooled normal plasma was incubated for 2 min at room temperature in the absence (open circles) or presence of polyP, after which clotting was initiated with calcium chloride. PolyP of different chain lengths was included at a final concentration of 75 µM phosphate equivalents. PolyP lengths used were: polyP$_{25}$ (open triangles); polyP$_{45}$ (filled triangles); polyP$_{65}$ (open squares); polyP$_{75}$ (filled circles). Results represent the mean of duplicate wells. These data are a representative example of 3 experiments.

The effect of polyP chain length on activation of clotting via the contact pathway was examined by pre-incubating PolyP of varying chain lengths with pooled normal plasma for 2 min, after which clotting was initiated with calcium chloride. As seen in FIG. 8, normal plasma incubated without polyP took more than 10 min to clot. Adding polyP$_{25}$ had no discernable effect on clotting time, but adding polyP$_{45}$, polyP$_{65}$ or polyP$_{75}$ dramatically shortened the clotting times (to less than 5 min; FIG. 8). These data indicate that, in order to enhance factor XII activation, polyP molecules preferably have a minimal chain length of between 25 and 45 phosphate residues.

PolyP Accelerates the Tissue Factor Pathway of Blood Clotting

Figure 9:
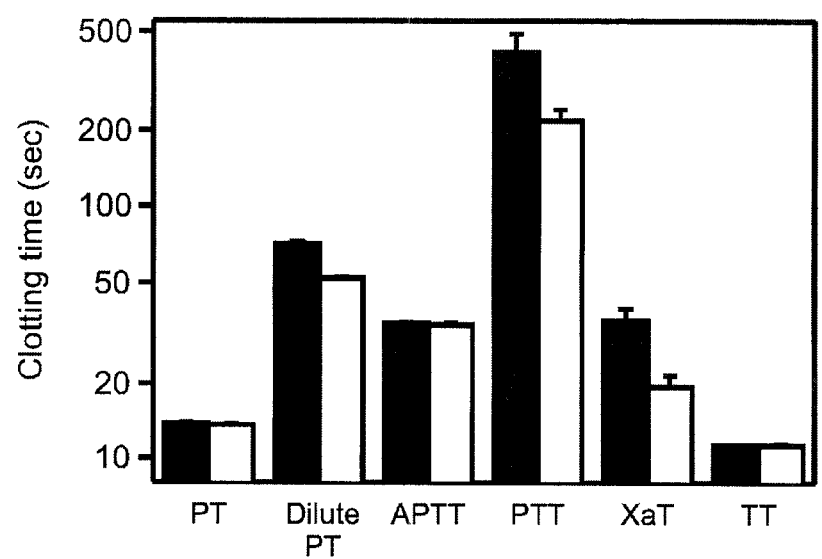
FIG. 9 is a bar graph showing the effect of polyP on various clotting tests. The indicated clotting assays were performed in a coagulometer with pooled normal plasma in the presence (open bars) or absence (filled bars) of 75 µM phosphate equivalents of polyP$_{75}$ added to the clotting reagents. Mean clotting times are depicted (error bars=standard deviation; n=5).

The ability of polyP$_{75}$ to influence the clotting time of a variety of clotting assays was systematically evaluated, employing commonly used plasma clotting assays including the prothrombin time (PT) assay, the partial thromboplastin time (PTT) assay, the activated partial thromboplastin time (aPTT) assay, a factor Xa clotting assay (XaT), and the thrombin time (TT) assay (FIG. 9). The PT assay, which is conducted by adding a thromboplastin reagent (a source of tissue factor activity and calcium ions) to plasma, drives coagulation through the extrinsic, or tissue factor pathway. The PTT and aPTT assays rely on the contact, or intrinsic, pathway of blood clotting. The XaT assay relies on the presence of factor V, prothrombin and fibrinogen in plasma, while the TT assay relies only on the presence of fibrinogen. Therefore, these assays assess different stages of the blood clotting cascades. All were performed in a coagulometer at 37° C.

As seen in FIG. 9, adding polyP$_{75}$ to plasma in a standard PT assay had little effect on clotting time. However, when the PT assay was modified to employ a dilute thromboplastin reagent (dilute PT assay), polyP$_{75}$ caused a small but reproducible shortening of the clotting time. PolyP$_{75}$ had no effect on the aPTT assay, but shortened the clotting time of the PTT assay. This result is consistent with polyP being a weak activator of the contact pathway of blood clotting, since the aPTT assay employs a potent activator of the contact pathway which is missing in the PTT assay. Interestingly, polyP$_{75}$ had no effect on the TT assay, but shortened the clotting time in the XaT assay. This latter result, together with the results from the dilute PT assay, suggest that polyP enhances some aspect of the tissue factor pathway of blood clotting upstream of thrombin.

Figure 10:
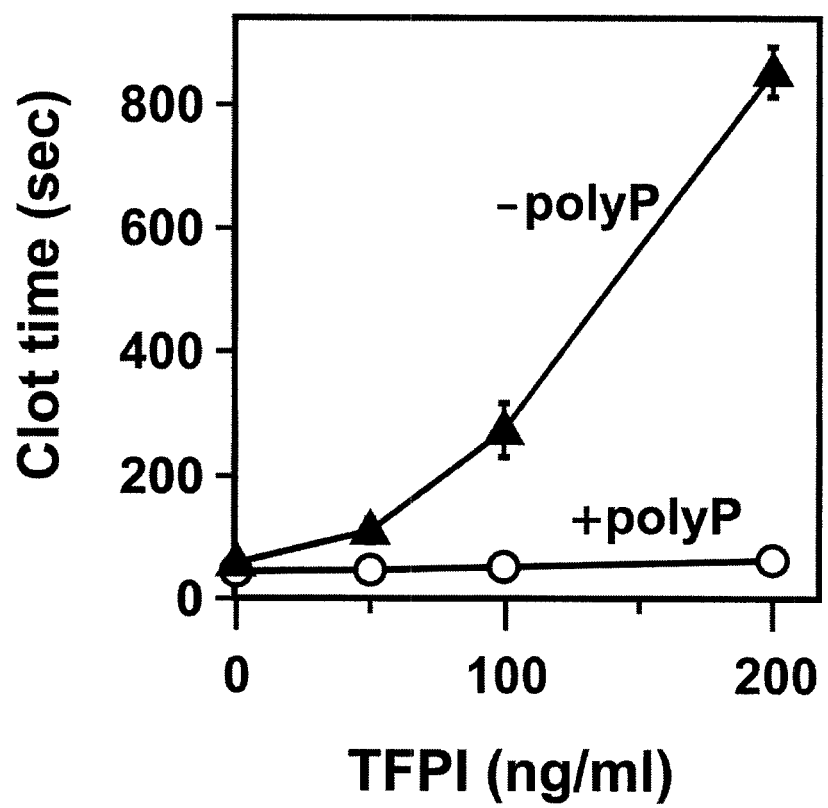
FIG. 10 is a graph showing that polyP abrogates the anticoagulant effect of TFPI. Varying concentrations of TFPI were added to pooled normal plasma and the clotting times were measured using the dilute PT assay in the presence (open circles) or absence (closed triangles) of 75 µM phosphate equivalents of polyP$_{75}$ added to the dilute thromboplastin reagent. Mean clotting times are depicted (error bars=standard deviation; n=3).

PolyP Accelerates the Tissue Factor Pathway by Potently Blocking the Anticoagulant Effect of TFPI The hypothesis that polyP might block the anticoagulant effect of TFPI was tested. This was examined in a dilute PT assay in which varying concentrations of recombinant TFPI were added to plasma samples. Plasma normally contains relatively low levels of free TFPI, so adding exogenous TFPI can dramatically lengthen PT clotting times. As seen in FIG. 10, adding 50, 100 or 200 ng/ml TFPI to pooled normal plasma greatly prolonged the dilute PT clotting time. In striking contrast, inclusion of 75 μM polyP$_{75}$ phosphate equivalents in the dilute thromboplastin reagent completely abrogated the anticoagulant effect of TFPI at all TFPI concentrations tested. In other experiments, it was found that polyP$_{75}$ also abrogated the effect of TFPI in standard PT assays, although the absolute differences in clotting times with or without TFPI were smaller due to the very short baseline clotting times in standard PT assays (data not shown). Another plasma protease inhibitor capable of inactivating factor Xa is the serpin, antithrombin (formerly known as antithrombin III). Similar experiments using varying quantities of antithrombin added to antithrombin-deficient plasma in clotting assays to which polyP$_{75}$ was added revealed that polyP does not block the anticoagulant function of antithrombin (data not shown).

Figure 11:
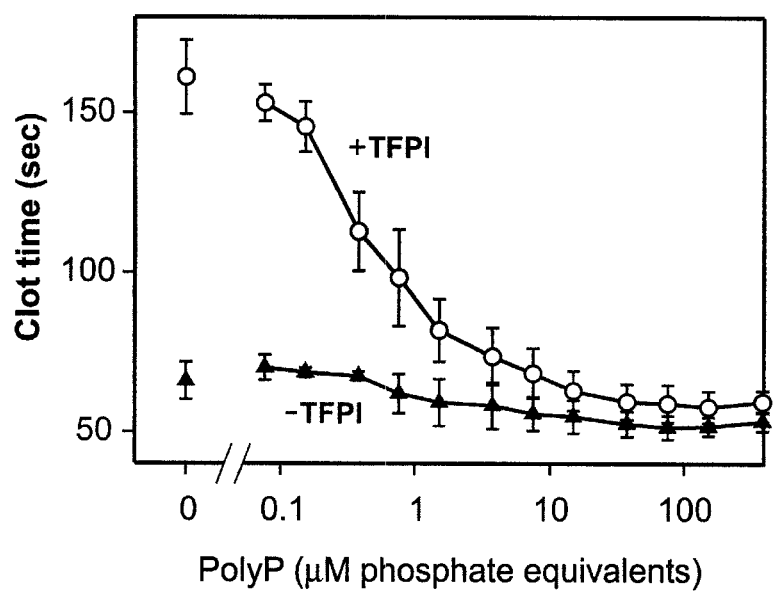
FIG. 11 is a graph showing that abrogation of the anticoagulant effect of TFPI by polyP is concentration-dependent. Varying concentrations of polyP$_{75}$ as phosphate equivalents were added to the dilute thromboplastin reagent. Clotting times were measured by the dilute PT assay using pooled normal plasma without added TFPI (closed triangles) or with 100 ng/ml TFPI (open circles). Mean clotting times are depicted (error bars=standard deviation; n=3).

The ability of polyP$_{75}$ to abrogate the anticoagulant effect of TFPI is concentration-dependent. When 100 ng/ml TFPI was added to pooled normal plasma, the dilute PT clotting time was increased from 66 sec to over 160 sec (FIG. 11). Adding increasing concentrations of polyP$_{75}$ to the dilute thromboplastin reagent progressively antagonized the ability of TFPI to prolong the clotting time. Interestingly, a significant shortening of the TFPI-prolonged clotting time was observed with as little as 375 nM phosphate equivalents of polyP, while the anticoagulant effect of TFPI was essentially completely abrogated at polyP$_{75}$ concentrations ranging from approximately 7500 nM phosphate equivalents to 375 μM phosphate equivalents. (It should be pointed out that the polyP concentrations given here are the concentrations added to the thromboplastin reagent; since the thromboplastin reagent made up only one-third of the final volume in the clotting assays, the final concentrations of polyP$_{75}$ in clotting mixtures were threefold lower than indicated.)

Figure 12:
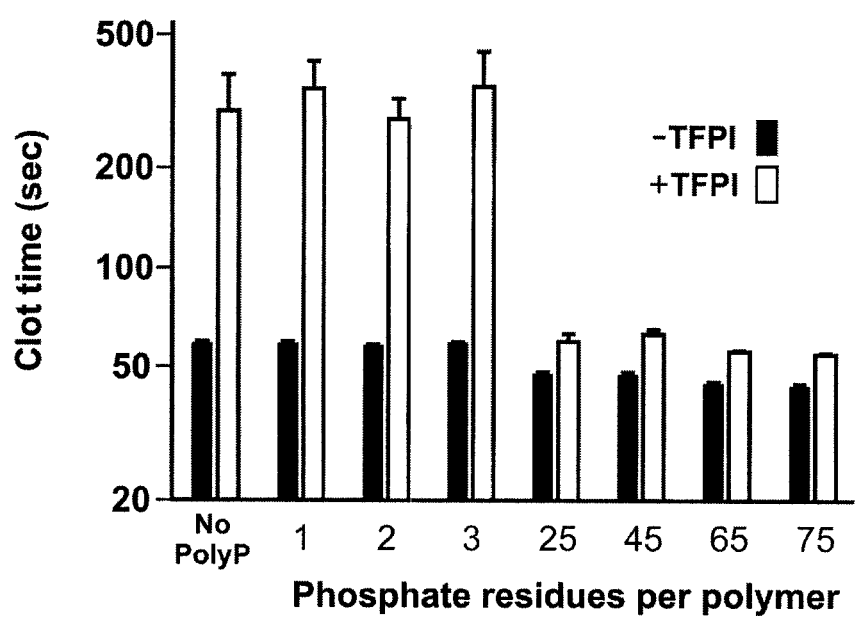
FIG. 12 is a bar graph showing that the ability of polyP to antagonize the anticoagulant effect of TFPI depends upon chain length. Dilute PT assays were performed on pooled normal plasma samples, some of which contained 200 ng/ml TFPI (open bars) and some of which did not (filled bars).

The ability of polyP to block the effect of TFPI was also dependent upon polyP chain length. Dilute PT assays were performed on pooled normal plasma samples, some of which contained 200 ng/ml TFPI. In the absence of polyP, the addition of TFPI prolonged the mean clotting time from 59 sec to 294 sec. PolyP of the indicated chain lengths were included in the dilute thromboplastin reagent at concentrations of 75 μM phosphate equivalents. PolyP$_{25}$, PolyP$_{45}$, PolyP$_{65}$ and PolyP$_{75}$ all abrogated the anticoagulant effect of the TFPI (FIG. 12). On the other hand, very short phosphate molecules (P$_i$, PP$_i$, or polyP$_3$) did not block TFPI anticoagulant function at all. The size-dependence of polyP abrogation of TFPI function therefore differs from the size-dependence of polyP inhibition of fibrinolysis or activation of the contact pathway of blood coagulation. Thus, polyP$_{25}$ had the same ability to block TFPI function as did longer polyP molecules. In contrast, polyP$_{25}$ exhibited no ability to trigger the contact pathway and attenuated ability to inhibit fibrinolysis, relative to polyP molecules consisting of 45 or more phosphate units. This result means that it is possible to employ polyP molecules of varying polymer lengths to differentially modulate TFPI function versus fibrinolysis or contact activation.

Figure 13:
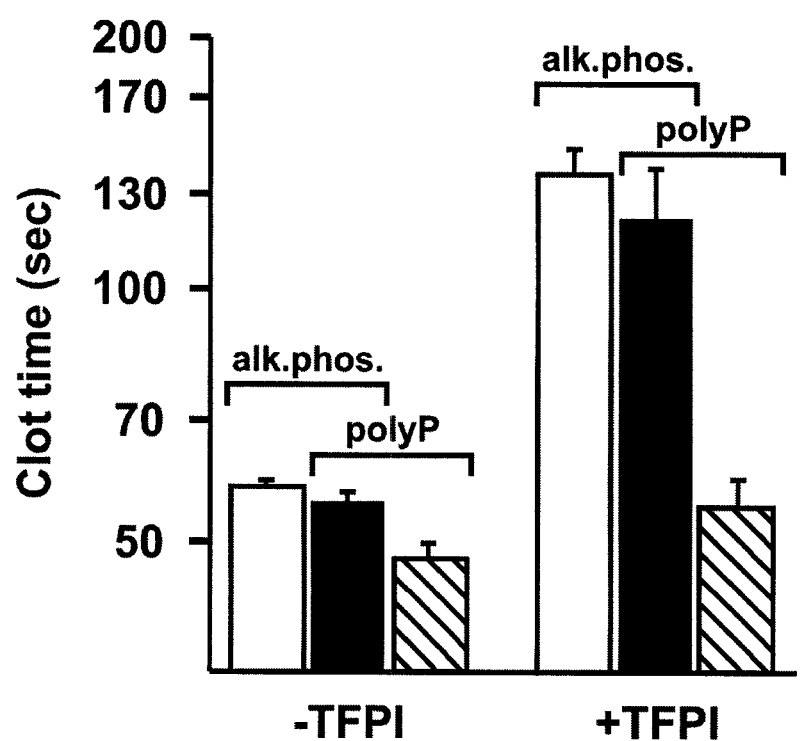
FIG. 13 is a bar graph showing that phosphatase digestion of polyP eliminates its ability to reverse the anticoagulant effect of TFPI. PolyP$_{65}$ was incubated at room temperature with or without calf intestinal alkaline phosphatase, and dilute PT clotting times were measured using pooled normal plasma with or without added TFPI. With alkaline phosphatase but no polyP (white bars); with phosphatase and polyP$_{65}$ (black bars); and with polyP but no alkaline phosphatase (lined bars). Data are mean clotting times (error bars=standard deviation; n=3).

To further underscore the size-dependence of polyP in antagonizing TFPI function, polyP$_{65}$ was extensively digested with calf intestine alkaline phosphatase. Previous studies have shown that mammalian intestine alkaline phosphatase is also a highly active exopolyphosphatase [14]. Adding 100 ng/ml TFPI to pooled normal plasma substantially prolonged its dilute PT clotting time, and adding 1300 nM phosphate equivalents of polyP$_{65}$ abrogated this prolongation (FIG. 13). After polyP$_{65}$ was digested for 2 hr with alkaline phosphatase, however, it was rendered completely ineffective in blocking the TFPI-mediated prolongation of the dilute PT clotting assay (FIG. 13). This experiment confirms that short phosphate molecules cannot block the anticoagulant effect of TFPI, and furthermore it demonstrates that the ability of polyP to abrogate the effect of TFPI is not due to contaminant(s) present in the polyP preparations.

Stability of PolyP in Human Plasma and Serum

Figure 14:
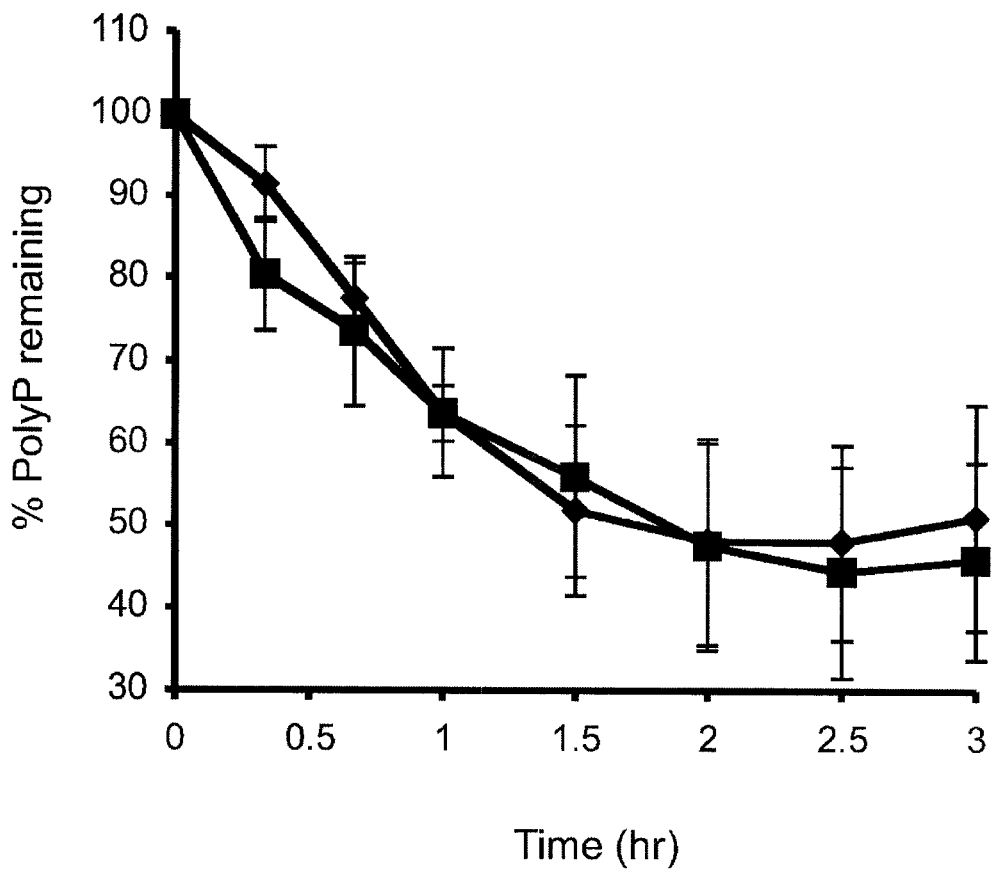
FIG. 14 is a graph showing the stability of polyP in plasma and serum. PolyP$_{75}$ was incubated in human serum (squares) or heparinized plasma (diamonds), and at different time points aliquots were taken and the remaining polyP was determined.
Figure 15:
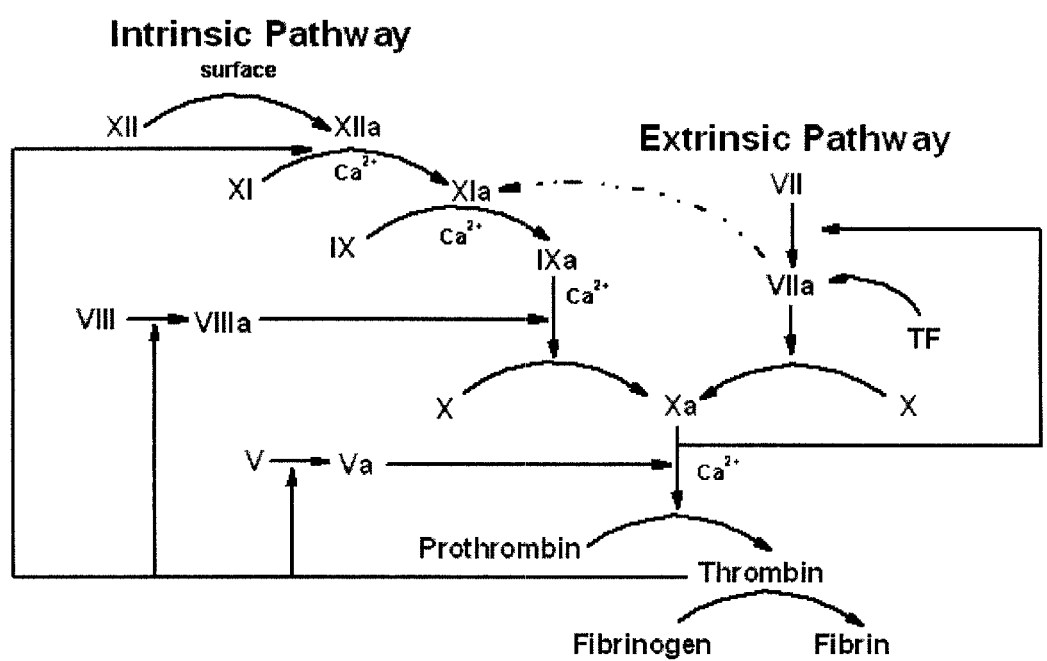
FIG. 15 is a schematic of the clotting cascades.

To investigate the stability of polyP, polyP$_{75}$ was incubated at a final concentration of 10 mM phosphate equivalents in human plasma or serum at 37° C. and the remaining polyP was quantified at varying times thereafter. The results (FIG. 14) revealed that degradation of polyP$_{75}$ was slow, with a 50% degradation at about 2 hours. This is in agreement with a previous report on the slow degradation of polyP$_{34}$ in the presence of human plasma or serum [15].

Materials & Methods

Materials—Pooled normal plasma and factor XII-deficient plasma were obtained from George King Bio-Medical, Inc. (Overland Park, Kans.). Human plasmas immunodepleted of TAFI or antithrombin were from Affinity Biologicals (Ancaster, Ontario, Canada). PolyP of mean chain lengths 25, 45, 65 or 75 (sodium phosphate glass) was obtained from Sigma Chemical Company (St. Louis, Mo.). CPI and tPA were obtained from Calbiochem (San Diego, Calif.), while uPA was a kind gift of J. Henkin (Abbott Laboratories). Human alpha thrombin, antithrombin, and factor Xa were from Enzyme Research Laboratories (South Bend, Ind.). Recombinant, full-length human TFPI was a kind gift of Dr. George Broze, Washington University St. Louis.

Microplate-based assays of plasma clotting and fibrinolysis—Some of the clotting assays were conducted in flat-bottom, polystyrene, 96-well plates (Corning). Turbidity, a measure of clot formation, was quantified at 37° C. by measuring the absorbance of light at 405 nm in a VERSAmax microplate reader (Molecular Devices, Sunnyvale, Calif.). Reactions (100 μl final volume) typically contained the following final concentrations: 30% (v/v) human plasma; 8 mM Tris-HCl buffer, pH 7.4; 0.008% (v/v) Tween-20; 10.6 mM calcium chloride; and, variably, 10 nM thrombin. In some experiments, clotting reactions were initiated by calcium ions alone. In this case, a 1.25× reaction mixture of the above-described components (except calcium chloride) was prepared in a final volume of 80 μl per well. Clotting was then initiated by adding 20 μl of 53 mM calcium chloride and absorbance at 405 nM was monitored. In other experiments, clotting was initiated by a mixture of calcium ions and thrombin. In these cases, to the 80 μl reaction mixtures described above were added 10 μl of 106 mM calcium chloride followed immediately by 10 μl of 100 nM thrombin.

Combined plasma clotting/fibrinolysis assays were also performed in 96-well plates as described in the previous paragraph, except that the reaction mixtures included 1.4 nM uPA to stimulate fibrinolysis.

Unless otherwise stated, polyP$_{75}$ was typically included in these clotting or clotting/fibrinolysis assays at a final concentration of 75 μM phosphate equivalents in the clotting reaction. When polyP preparations of other chain lengths were studied, they were also typically used at final concentrations of 75 μM phosphate equivalents. Thus, polyP$_{25}$ was used at a final concentration of 3 μM, polyP$_{45}$ was used at a final concentration of 1.67 μM, and polyP$_{65}$ was used at a final concentration of 1.15 μM. When present, CPI was used at a final concentration of 6.25 μM CPI.

Coagulometer-based plasma clotting assays—Recombinant human tissue factor was reconstituted into phospholipid vesicles as previously described [18], using a mixture of 20% phosphatidylserine and 80% phosphatidylcholine at a phospholipid:tissue factor molar ratio of 8700:1. Blank phospholipid vesicles (PCPS vesicles) composed of 20% phosphatidylserine and 80% phosphatidylcholine (and no tissue factor) were prepared as described [18]. The thromboplastin reagent for the PT assay was prepared by diluting relipidated tissue factor to a final concentration of 200 ng/ml tissue factor in TBSA buffer (50 mM Tris-HCl pH 7.5, 100 mM NaCl, 0.02% sodium azide, 0.1% (w/v) bovine serum albumin). The thromboplastin reagent for the dilute PT assay was prepared in the same manner as the reagent for the PT assay, except that the relipidated tissue factor was typically diluted to a final concentration of 1 ng/ml tissue factor in TBSA buffer containing 50 μM PCPS vesicles. The aPTT reagent was STA®-PTT (Diagnostica Stago, Parsippany, N.J.). The PTT reagent consisted of 50 µM PCPS vesicles in TBSA buffer. The clotting reagent for the XaT assay consisted of 1 nM factor Xa in TBSA buffer containing 50 µM PCPS vesicles. The TT reagent consisted of 5 units/ml thrombin in TBSA buffer containing 16.7 mM calcium chloride.

The PT, XaT, aPTT and PTT clotting assays were typically performed in a STart coagulometer (Diagnostica Stago) by pre-incubating 50 µl of human plasma with 50 µl of the indicated clotting reagent at 37° C. for the following times: PT and XaT assays, 120 sec; aPTT and PTT assays, 180 sec. Clotting was then initiated by adding 50 µl of 25 mM calcium chloride solution that had been pre-warmed to 37° C. The time to clot formation was then measured relative to the point of addition of calcium chloride. The TT clotting assay was performed in the same coagulometer as follows: 50 µl human plasma was pre-warmed to 37° C. for 60 sec, after which 50 µl of pre-warmed TT reagent was added and the time to clot formation was measured. When the effect of TFPI on clotting was tested, TFPI was added to plasma at the indicated concentration immediately before use. When the effect of polyP on clotting was tested, polyP was added to the clotting reagent at the indicated concentration. In all but the TT assay, the clotting reagent contributed one-third of the total volume in the clotting reaction. For this reason, the final polyP concentrations in the clotting reactions were typically threefold lower than indicated (or twofold lower for the TT assay).

Digestion of polyP with alkaline phosphatase—100 µM PolyP$_{65}$ was digested for 2 hr at room temperature by 100 U/ml calf intestinal alkaline phosphatase (Promega, Madison, Wis.) in 50 mM Tris-HCl buffer, pH 9.5. The digested polyP was used immediately in clotting reactions by diluting the digestion mixture into dilute thromboplastin reagent to yield a final polyP$_{65}$ concentration of 200 nM.

PolyP determination—Perchloric acid extraction and measurement of polyP after its incubation with human serum or heparinized plasma was performed as described [3].

REFERENCES

1. Kornberg, A. Inorganic polyphosphate: Toward making a forgotten polymer unforgettable. J Bacteriol. 177: 491-496 (1995).
2. Docampo, R., de Souza, W., Miranda, K., Rohloff, P. & Moreno, S, N. J. Acidocalcisomes—conserved from bacteria to man. Nature Rev. Microbiol., 3:251-61 (2005).
3. Ruiz, F. A., Lea, C. R., Oldfield, E. & Docampo, R. Human platelet dense granules contain polyphosphate and are similar to acidocalcisomes of bacteria and unicellular eukaryotes. J Biol. Chem. 279: 44250-44257 (2004).
4. Dano, K., Andreasen, P. A., Grondahl-Hansen, J., Kristensen, P., Nielsen, L. S. & Skriver, L. Plasminogen activators, tissue degradation, and cancer. Adv. Cancer Res. 44: 139-266 (1985).
5. Bajzar, L., Morser, J. & Nesheim, M. TAFI, or plasma procarboxypeptidase B, couples the coagulation and fibrinolytic cascades through the thrombin-thrombomodulin complex. J Biol. Chem. 271: 16603-16608 (1996).
6. Nesheim, M., Wang, W., Boffa, M., Nagashima, M., Morser, J. & Bajzar, L. Thrombin, thrombomodulin and TAFI in the molecular link between coagulation and fibrinolysis. Thromb Haemost 78: 386-391 (1997).
7. Nesheim, M. Thrombin and fibrinolysis. Chest 124: 33S-39S (2003).
8. Bajzar, L., Jain, N., Wang, P. & Walker, J. B. Thrombin activatable fibrinolysis inhibitor: not just an inhibitor of fibrinolysis. Crit Care Med. 32: S320-S324 (2004).
9. Schneider, M., Boffa, M., Stewart, R., Rahman, M., Koschinsky, M. & Nesheim, M. Two naturally occurring variants of TAFI (Thr-325 and Ile-325) differ substantially with respect to thermal stability and antifibrinolytic activity of the enzyme. J Biol. Chem. 277: 1021-1030 (2002).
10. Boffa, M. B., Bell, R., Stevens, W. K. & Nesheim, M. E. Roles of thermal instability and proteolytic cleavage in regulation of activated thrombin-activable fibrinolysis inhibitor. J Biol. Chem. 275: 12868-12878 (2000).
11. Marx, P. F., Hackeng, T. M., Dawson, P. E., Griffin, J. H., Meijers, J. C. & Bouma, B. N. Inactivation of active thrombin-activable fibrinolysis inhibitor takes place by a process that involves conformational instability rather than proteolytic cleavage. J Biol. Chem. 275: 12410-12415 (2000).
12. Marx, P. F., Dawson, P. E., Bouma, B. N. & Meijers, J. C. Plasmin-mediated activation and inactivation of thrombin-activatable fibrinolysis inhibitor. Biochemistry 41: 6688-6696 (2002).
13. Rojkjaer, R. & Schmaier, A. H. Activation of the plasma kallikrein/kinin system on endothelial cell membranes. Immunopharmacology 43: 109-114 (1999).
14. Lorenz, B. & Schroder, H. C. Mammalian intestinal alkaline phosphatase acts as highly active exopolyphosphatase. Biochim. Biophys. Acta 1547: 254-261 (2001).
15. Lorenz, B., Leuck, J., Kohl, D., Muller, W. E. & Schroder, H. C. Anti-HIV-1 activity of inorganic polyphosphates. J. Acquir. Immune. Defic. Syndr. Hum. Retrovirol. 14: 110-118 (1997).
16. Mosnier, L. O., Buijtenhuijs, P., Marx, P. F., Meijers, J. C. & Bouma, B. N. Identification of thrombin activatable fibrinolysis inhibitor (TAFI) in human platelets. Blood 101: 4844-4846 (2003).
17. Novotny, W. F., Girard, T. J., Miletich, J. P. & Broze, G. J., Jr. Platelets secrete a coagulation inhibitor functionally and antigenically similar to the lipoprotein associated coagulation inhibitor. Blood 72: 2020-2025 (1988).
18. Smith, S. A. & Morrissey, J. H. Rapid and efficient incorporation of tissue factor into liposomes. J Thromb Haemost 2: 1155-1162 (2004).
19. U.S. Pat. No. 6,319,896 (2001).
20. U.S. Pat. No. 6,323,326 (2001).
21. U.S. Pat. No. 5,888,968 (1999).
22. Kemball-Cook, G., Garner, I., Imanaka, Y., Nishimura, T., O'Brien, D. P., Tuddenham, E. G., McVey, J. H. High-level production of human blood coagulation factors VII and XI using a new mammalian expression vector. Gene. 139(2): 275-279 (1994).
23. Van Den Besselaar, A. M., Tripodi, A., Poller, L. WHO guidelines for thromboplastins and plasma used to control oral anticoagulation therapy. Annex 3. World Health Organ Tech Rep Ser. 889: 64-93 (1999).
24. Broze, G. J., Jr. Tissue factor pathway inhibitor. Thromb. Haemost. 74: 90-93 (1995).
25. Sandset, P. M., Abildgaard, U, Larsen, M. L. Heparin induces release of extrinsic coagulation pathway inhibitor (EPI). Thromb. Res. 50: 803-13 (1988).
26. Hansen, J.-B., Svensson, B., Sandset, P. M., Thijssen, F. Reduction of factor FVIIa activity during heparin therapy evidence for assay interactions with tissue factor pathway inhibitor and antithrombin. Thromb. Res. 100: 389-396 (2000).
27. Bladbjerg, E. M., Larsen, L. F., Østergaard, P., Jespersen, J. In vitro effects of heparin and tissue factor pathway inhibitor on factor VII assays. Possible implications for measurements in vivo after heparin therapy. Blood Coagul. Fibrinolysis 11: 739-745 (2000).
28. Jespersen, J., Bertina, R. M., Haverkate, F. (eds) Laboratory Techniques in Thrombosis: A Manual. $2^{nd}$ revised edition of ECAT Assay Procedures. Kluwer Academic Publishers, Dordrecht (1999).

What is claimed is:

1. A method of stopping or slowing bleeding from a wound, comprising contacting blood from the wound at the site of the wound with a composition comprising (i) polyphosphate (polyP$_n$), wherein n is at least 25, and (ii) a pharmaceutical carrier.

2. The method of claim 1, wherein the composition is in unit dosage form.

3. The method of claim 1, wherein the pharmaceutical carrier comprises a solid support.

4. A method of claim 1, wherein the composition is sterile.

5. A method of stopping or slowing bleeding from a wound, comprising contacting blood from the wound at the site of the wound with polyphosphate (polyP$_n$), wherein n is at least 25.

6. A method of blocking Tissue Factor Pathway Inhibitor (TFPI) in a clotting assay, comprising administering polyphosphate (polyP$_n$) as an activator of clotting in an assay composition comprising TFPI, wherein n is at least 25.

7. The method of claim 6, wherein the composition comprises a thromboplastin reagent.

8. A method of blocking Tissue Factor Pathway Inhibitor (TFPI) in a wound, comprising contacting blood from the wound at the site of the wound with a composition comprising polyphosphate (polyP$_n$), wherein n is at least 25.

* * * * *

UNITED STATES PATENT AND TRADEMARK OFFICE
CERTIFICATE OF CORRECTION

PATENT NO. : 9,597,375 B2  
APPLICATION NO. : 12/582595  
DATED : March 21, 2017  
INVENTOR(S) : Morrissey et al.

It is certified that error appears in the above-identified patent and that said Letters Patent is hereby corrected as shown below:

On the Title Page

In Column 1, under item (73), please delete "Illinios" and replace with "Illinois".

Signed and Sealed this  
Twenty-second Day of August, 2017

Joseph Matal  
*Performing the Functions and Duties of the*  
*Under Secretary of Commerce for Intellectual Property and*  
*Director of the United States Patent and Trademark Office*